(12) United States Patent
Dala-Krishna

(10) Patent No.: US 8,622,915 B2
(45) Date of Patent: *Jan. 7, 2014

(54) ULTRASOUND IMAGE PROCESSING TO RENDER THREE-DIMENSIONAL IMAGES FROM TWO-DIMENSIONAL IMAGES

(75) Inventor: Praveen Dala-Krishna, Sicklerville, NJ (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/290,696

(22) Filed: Nov. 7, 2011

(65) Prior Publication Data

US 2012/0113108 A1 May 10, 2012

Related U.S. Application Data

(63) Continuation of application No. 11/772,161, filed on Jun. 30, 2007, now Pat. No. 8,057,394.

(51) Int. Cl.
*A61B 8/14* (2006.01)

(52) U.S. Cl.
USPC ............................. 600/466; 600/437

(58) Field of Classification Search
None
See application file for complete search history.

(56) References Cited

U.S. PATENT DOCUMENTS

| | | |
|---|---|---|
| 4,161,121 A | 7/1979 | Zitelli et al. |
| 4,241,610 A | 12/1980 | Anderson |
| 4,462,408 A | 7/1984 | Silverstein et al. |
| 4,519,260 A | 5/1985 | Fu et al. |
| 4,576,177 A | 3/1986 | Webster |
| 4,605,009 A | 8/1986 | Pourcelot et al. |
| 4,841,977 A | 6/1989 | Griffith et al. |
| 4,890,268 A | 12/1989 | Smith et al. |
| 4,917,097 A | 4/1990 | Proudian et al. |
| 4,951,677 A | 8/1990 | Crowley et al. |
| 5,002,059 A | 3/1991 | Crowley et al. |
| 5,090,956 A | 2/1992 | McCoy |
| 5,105,819 A | 4/1992 | Wollschlager et al. |
| 5,152,294 A | 10/1992 | Mochizuki et al. |
| 5,158,087 A | 10/1992 | Gatzke |
| 5,170,793 A | 12/1992 | Takano et al. |
| 5,195,968 A | 3/1993 | Lundquist et al. |
| 5,254,088 A | 10/1993 | Lundquist et al. |
| 5,279,559 A | 1/1994 | Barr |
| 5,307,816 A | 5/1994 | Hashimoto et al. |
| 5,309,914 A | 5/1994 | Iinuma |
| 5,325,860 A | 7/1994 | Seward et al. |
| 5,336,182 A | 8/1994 | Lundquist et al. |
| 5,345,938 A | 9/1994 | Nishiki et al. |
| 5,345,940 A | 9/1994 | Seward et al. |
| 5,357,550 A | 10/1994 | Asahina et al. |
| 5,358,478 A | 10/1994 | Thompson et al. |
| 5,364,351 A | 11/1994 | Heinzelman et al. |

(Continued)

*Primary Examiner* — Long V. Le
*Assistant Examiner* — Angela M Hoffa
(74) *Attorney, Agent, or Firm* — Dykema Gossett PLLC

(57) ABSTRACT

Methods for processing two-dimensional ultrasound images from an intracardiac ultrasound imaging catheter provide improved image quality and enable generating three-dimensional composite images of the heart. Two-dimensional ultrasound images are obtained and stored in conjunction with correlating information, such as time or an electrocardiogram. Images related to particular conditions or configurations of the heart can be processed in combination to reduce image noise and increase resolution. Images may be processed to recognize structure edges, and the location of structure edges used to generate cartoon rendered images of the structure. Structure locations may be averaged over several images to remove noise, distortions and blurring from movement.

27 Claims, 14 Drawing Sheets

(56) References Cited

U.S. PATENT DOCUMENTS

| | | | | |
|---|---|---|---|---|
| 5,372,138 | A | 12/1994 | Crowley et al. | |
| 5,385,148 | A | 1/1995 | Lesh et al. | |
| 5,395,327 | A | 3/1995 | Lundquist et al. | |
| 5,438,997 | A | 8/1995 | Sieben et al. | |
| 5,456,258 | A | 10/1995 | Kondo et al. | |
| 5,456,664 | A | 10/1995 | Heinzelman et al. | |
| 5,470,350 | A | 11/1995 | Buchholtz et al. | |
| 5,499,630 | A | 3/1996 | Hiki et al. | |
| 5,515,853 | A | 5/1996 | Smith et al. | |
| 5,515,856 | A | 5/1996 | Olstad et al. | |
| 5,531,686 | A | 7/1996 | Lundquist et al. | |
| 5,560,362 | A | 10/1996 | Sliwa et al. | |
| 5,588,432 | A | 12/1996 | Crowley et al. | |
| 5,622,174 | A | 4/1997 | Yamazaki | |
| 5,662,116 | A | 9/1997 | Kondo et al. | |
| 5,697,965 | A | 12/1997 | Griffin | |
| 5,699,805 | A | 12/1997 | Seward et al. | |
| 5,701,897 | A | 12/1997 | Sano | |
| 5,704,361 | A | 1/1998 | Seward et al. | |
| 5,713,363 | A | 2/1998 | Seward et al. | |
| 5,715,817 | A | 2/1998 | Stevens-Wright et al. | |
| 5,722,403 | A | 3/1998 | McGee et al. | |
| 5,749,364 | A | 5/1998 | Sliwa et al. | |
| 5,788,636 | A | 8/1998 | Curley | |
| 5,795,299 | A | 8/1998 | Eaton et al. | |
| 5,797,848 | A | 8/1998 | Marian et al. | |
| 5,800,356 | A | 9/1998 | Criton | |
| 5,807,324 | A | 9/1998 | Griffin | |
| 5,846,205 | A | 12/1998 | Curley et al. | |
| 5,888,577 | A | 3/1999 | Griffin et al. | |
| 5,891,088 | A | 4/1999 | Thompson et al. | |
| 5,906,579 | A | 5/1999 | Vander Salm et al. | |
| 5,916,168 | A | 6/1999 | Pedersen et al. | |
| 5,921,978 | A | 7/1999 | Thompson et al. | |
| 5,928,276 | A | 7/1999 | Griffin et al. | |
| 5,931,863 | A | 8/1999 | Griffin et al. | |
| 5,935,102 | A | 8/1999 | Bowden et al. | |
| 5,938,616 | A | 8/1999 | Eaton et al. | |
| 5,954,654 | A | 9/1999 | Eaton et al. | |
| 6,013,072 | A | 1/2000 | Winston et al. | |
| 6,033,378 | A | 3/2000 | Lundquist et al. | |
| 6,039,693 | A | 3/2000 | Seward et al. | |
| 6,085,117 | A | 7/2000 | Griffin et al. | |
| 6,144,870 | A | 11/2000 | Griffin | |
| 6,171,248 | B1 * | 1/2001 | Hossack et al. | 600/459 |
| 6,173,205 | B1 | 1/2001 | Griffin et al. | |
| 6,190,353 | B1 | 2/2001 | Makower et al. | |
| 6,210,333 | B1 | 4/2001 | Gardner et al. | |
| 6,224,556 | B1 | 5/2001 | Schwartz et al. | |
| 6,228,032 | B1 | 5/2001 | Eaton et al. | |
| 6,261,246 | B1 | 7/2001 | Pantages et al. | |
| 6,293,943 | B1 | 9/2001 | Panescu et al. | |
| 6,306,096 | B1 | 10/2001 | Seward et al. | |
| 6,306,097 | B1 | 10/2001 | Park et al. | |
| 6,310,828 | B1 | 10/2001 | Mumm et al. | |
| 6,358,208 | B1 | 3/2002 | Lang et al. | |
| 6,360,027 | B1 | 3/2002 | Hossack et al. | |
| 6,368,275 | B1 | 4/2002 | Sliwa et al. | |
| 6,385,489 | B1 | 5/2002 | Griffin et al. | |
| 6,398,731 | B1 | 6/2002 | Mumm et al. | |
| 6,423,002 | B1 | 7/2002 | Hossack | |
| 6,440,488 | B2 | 8/2002 | Griffin et al. | |
| 6,443,894 | B1 | 9/2002 | Sumanaweera et al. | |
| 6,475,148 | B1 | 11/2002 | Jackson et al. | |
| 6,475,149 | B1 | 11/2002 | Sumanaweera | |
| 6,482,161 | B1 | 11/2002 | Sumanaweera et al. | |
| 6,485,455 | B1 | 11/2002 | Thompson et al. | |
| 6,491,633 | B1 | 12/2002 | Krishnan et al. | |
| 6,503,202 | B1 | 1/2003 | Hossack et al. | |
| 6,517,488 | B1 | 2/2003 | Hossack | |
| 6,527,717 | B1 * | 3/2003 | Jackson et al. | 600/437 |
| 6,532,378 | B2 | 3/2003 | Saksena et al. | |
| 6,554,770 | B1 | 4/2003 | Sumanaweera et al. | |
| 6,589,182 | B1 | 7/2003 | Loftman et al. | |
| 6,605,043 | B1 | 8/2003 | Dreschel et al. | |
| 6,607,488 | B1 | 8/2003 | Jackson et al. | |
| 6,607,528 | B1 | 8/2003 | Quick et al. | |
| 6,612,992 | B1 | 9/2003 | Hossack et al. | |
| 6,645,147 | B1 | 11/2003 | Jackson et al. | |
| 6,648,875 | B2 | 11/2003 | Simpson et al. | |
| 6,650,927 | B1 | 11/2003 | Keidar | |
| 6,709,396 | B2 | 3/2004 | Flesch et al. | |
| 6,773,402 | B2 | 8/2004 | Govari et al. | |
| 6,908,434 | B1 | 6/2005 | Jenkins et al. | |
| 6,923,768 | B2 | 8/2005 | Camus et al. | |
| 7,314,446 | B2 * | 1/2008 | Byrd et al. | 600/443 |
| 7,673,606 | B2 | 3/2010 | Ng et al. | |
| 7,697,974 | B2 * | 4/2010 | Jenkins et al. | 600/428 |
| 7,713,210 | B2 * | 5/2010 | Byrd et al. | 600/459 |
| 8,057,394 | B2 * | 11/2011 | Dala-Krishna | 600/466 |
| 8,228,028 | B2 | 7/2012 | Schneider | |
| 2003/0045796 | A1 | 3/2003 | Friedman | |
| 2003/0158483 | A1 * | 8/2003 | Jackson et al. | 600/449 |
| 2004/0097805 | A1 | 5/2004 | Verard et al. | |
| 2004/0249282 | A1 * | 12/2004 | Olstad | 600/437 |
| 2005/0080336 | A1 | 4/2005 | Byrd et al. | |
| 2005/0203390 | A1 | 9/2005 | Torp et al. | |
| 2005/0228290 | A1 | 10/2005 | Borovsky et al. | |
| 2006/0122514 | A1 | 6/2006 | Byrd et al. | |
| 2008/0146941 | A1 * | 6/2008 | Dala-Krishna | 600/466 |
| 2008/0146942 | A1 * | 6/2008 | Dala-Krishna | 600/466 |
| 2012/0113108 | A1 * | 5/2012 | Dala-Krishna | 345/419 |

\* cited by examiner

ULTRASOUND IMAGE PROCESSING TO RENDER THREE-DIMENSIONAL IMAGES FROM TWO-DIMENSIONAL IMAGES

RELATED APPLICATIONS

This application is a continuation of application Ser. No. 11/772,161, filed Jun. 30, 2007, now issued as U.S. Pat. No. 8,057,394.

BACKGROUND

The present invention relates to medical diagnostic systems and methods, and more particularly to methods for rendering three-dimensional images from two-dimensional images generated by an ultrasound imaging catheter system.

Recent advancements in miniaturization of ultrasound technology has enabled the commercialization of catheters including phased array ultrasound imaging transducers small enough to be positioned within a patient's body via intravenous cannulation. By imaging vessels and organs, including the heart, from the inside, such miniature ultrasound transducers have enabled physicians to obtain diagnostic images available by no other means.

Due largely to their small size, ultrasound imaging transducers used to image from the inside of the heart render two-dimensional slice image "frames". These image frames are generally bounded by the maximum imaging depth within an image scan angle. Typically, the scan angle is approximately 90 degrees, while the image depth depends upon the ultrasound frequency and the power.

While two-dimensional image frames provide very valuable diagnostic information, they require the clinician to mentally integrate many image frames taken at different rotational orientations in order to imagine how the heart appears in three-dimensions. In many medical circumstances, the clinician would benefit from being able to view the heart in three-dimensions.

While it has been suggested that two-dimensional ultrasound image frames may simply be stitched together to assemble three-dimensional images, a practical system for accomplishing this does not exist due to the difficulty of such image processing. Many factors, both physiological and technical, have prevented the combination and assembly of image frames with the degree of accuracy, detail and reliability required for cardiac diagnostic purposes.

SUMMARY

The present invention provides effective methods for processing and combining two-dimensional ultrasound image frames in order to generate three-dimensional and four-dimensional (three physical dimensions plus time) composite images and cines in normal cardiac cycles, as well as in diseased states, where the motion of the cardiac muscles might not be rhythmatic, and the frequency of such motion might not be within the spatial or temporal sampling capacity of the imaging set up. The embodiment methods include, but are not limited to, recognizing structure edges within ultrasound image frames using edge detection algorithms, and determining the coordinate locations of the detected structure edges. Nominal or average locations of heart structures are calculated by averaging (or other statistical measure) the coordinate locations of detected structure edges in multiple image frames obtained from the same viewing perspective. Averaging the coordinate locations of edges in multiple ultrasound images provides a single average location for structures that are moving during imaging. The averaged structure edges from images at a particular transducer rotational orientation are then combined with the averaged structure edges from images at other rotational orientations in order to generate a three-dimensional approximated cartoon rendering of heart structure within the imaged volume. Such methods can be combined with selective imaging or selecting images for processing based upon measured electrocardiogram signals to generate three-dimensional average cartoon renderings of heart structure at various points in the heartbeat cycle. Such three-dimensional average cartoon renderings datasets can be used to provide the clinician with an interactive display of heart structure.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain features of the invention.

DETAILED DESCRIPTION

Various embodiments of the present invention will be described in detail with reference to the accompanying drawings. Wherever possible, the same reference numbers will be used throughout the drawings to refer to the same or like parts or method steps.

As used herein, the terms "about" or "approximately" for any numerical values or ranges indicate suitable dimensional tolerances that allow the part or collection of components to function for their intended purposes as described herein. Also, as used herein, the term "patient" refers to any human or animal subject and is not intended to limit the systems or methods to human use. Further, embodiments of the invention will be described for use with an intracardiac ultrasound transducer array catheter. However, the embodiments may be applicable to any medical ultrasound transducer and are generally useful for ultrasound imaging of any portion of a patient's body.

Typical ultrasound imaging catheter systems, particularly intracardiac ultrasound imaging catheters, generate two dimensional sliced images of tissue, referred to as image frames, within the field of view of the transducer array. Since the ultrasound imaging catheter has a small diameter, such as about 6 to 10 French, it can be inserted into most organs of the body via catheterization through a vein or artery, or through small incisions such as in an arthroscopic procedure. For example, an intracardiac ultrasound catheter can be introduced into the heart through the vena cava to image the atria and ventricles from the inside. Such access of the imaging sensor provides image details and perspective that are available by no other imaging means.

Figure 1:
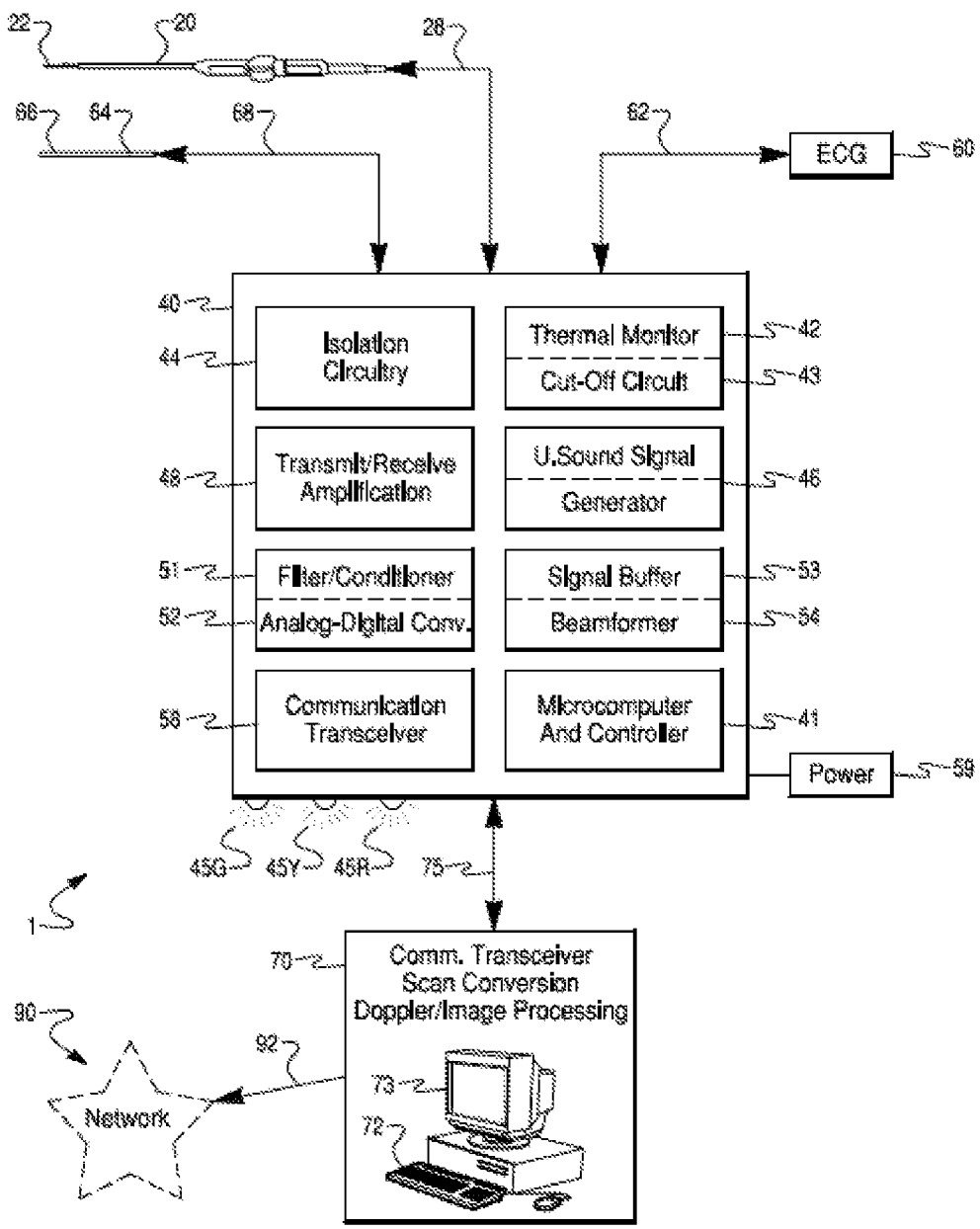
FIG. 1 is a block diagram of an intracardiac ultrasound imaging system.

The main elements of an embodiment of an intracardiac ultrasound imaging system are illustrated in FIG. 1. The illustrated system embodiment includes an ultrasound transducer array 22 carried by or positioned on a catheter 20 coupled to an ultrasound unit 40 by a signal cable 28. The ultrasound unit 40 is connected to a display, such as a display unit 70, by a data interface 75 which may be wired or wireless. Example ultrasound imaging system embodiments suitable for use with the present image processing method embodiments are disclosed in U.S. patent application Ser. No. 11/610,778, entitled "Integrated Beam Former And Isolation For An Ultrasound Probe" filed Dec. 14, 2006, the entire contents of which are hereby incorporated by reference.

A signal cable 28 delivers ultrasound signals from the ultrasound unit 40 to each of the transducers in the array 22. Typically, the signal cable 28 will include at least one wire per transducer, and in an embodiment, includes a coaxial cable connected to each transducer in the array 22. Typically, the signal cable 28 includes an electrical connection plug (e.g., a standard connector) on its proximal end. Providing a plug connector on the proximal end of the cable 28 allows completion of the many electrical connections between the cable conductors and the ultrasound unit 40 by pressing the plug into a complementary connector in the housing 100 of the ultrasound unit 40.

The transducers in the array 22 convert the electrical signals from the ultrasound unit 40 into sound waves, which propagate into a portion of a patient's anatomy, such as the heart. The same transducer array 22 also receives ultrasound echoes reflected from anatomic structures and transforms the received sound into electrical signals (e.g., by means of the piezoelectric effect). These electrical signals are conducted via cable 28 back to the ultrasound unit 40.

A signal generator 46 generates electrical signals of ultrasonic frequencies to be provided to the ultrasound transducer array 22. The signal generator 46 can be configured to produce signals of particular wave forms, frequencies and amplitudes as desired for imaging tissue. The signal generator 46 is configured to generate signals with the necessary transducer-to-transducer phase lag to enable the transducer array to generate a focused and steerable sound beam as is well known in the art of imaging ultrasound phased array transducers. Alternatively, phase lag may be added by another circuit, such as a beam former circuit 54.

A transmit/receive multiplexer circuit 48 can be included to direct the signals generated by the generator 46 to isolation circuitry 44 and to separate out echo signals returned from isolation circuitry 44 from the generated signals.

Isolation circuitry 44 is included to isolate unintended, potentially unsafe electrical currents and voltages from the transducer array 22 which contacts the patient. Also, a thermal monitoring circuit 42 and a cut-off circuit 43 may be included to mitigate possible risks to the patient that can result from excessive local heating by ultrasound. An example of such safety methods and systems is embodied in the ViewMate® catheter ultrasound system from EP MedSystems, Inc. of West Berlin, N.J.

A filter and conditioner circuit 51 can be included in the ultrasound unit 40 to reject spurious signals that may be induced in or through cable 28.

An analog-to-digital converter (ADC) 52 can be included in the ultrasound unit 40 to frequently sample and convert the ultrasound signals from analog electrical levels to discrete digital numeric values.

A signal buffer 53 can be included to store at least a portion of the echo signals, which are returned from the transducer array 22 and which may be processed by other elements of the ultrasound unit 40. In an embodiment, a signal buffer 53 is included to store the echo signals as digital data in a random-access semiconductor memory (RAM).

Beam former 54 circuits may be included to process signals sent to and received from the transducer array 22 to enable phased-array ultrasound imaging. The beam former 54 may receive ultrasound signals from the signal generator 46 and introduce phase lags for each transducer element so that when the signals are applied to the transducer elements a narrow beam of sound emanates from the array. Also, the beam former 54 may receive signals from the transducer array and process the ultrasound echo signal data to calculate the amplitude and direction of the ultrasound echoes returned to the transducer array 22 from each of many specific angles and distances. The beam former 54 may also determine the frequency or Doppler frequency shift of the signal returned form each of selected angles and distances from the transducer array 22.

In an embodiment associated with cardiac imaging, the ultrasound unit 40 may also include electrical connections for receiving signals from electrocardiogram (ECG) electrodes and for passing such signals on to an external electrocardiogram or electrophysiology unit 60 which may be connected to the ultrasound unit 40 through a communications interface 62. The communications interface 62 may be any wired or wireless interface. In an embodiment, the ECG electrodes can be an intracardiac electrophysiology catheter 64 which includes one or more electrodes 66 near a distal end for sensing electrical activity in the heart. Electrical signals sensed by the electrodes 66 can be conveyed to the ultrasound unit 40 by means of an extension of the catheter 64 or a connecting cable 68.

In an embodiment, signals sent by the ECG or electrophysiology unit 60 through the interface 62 can be recorded or used to synchronize ultrasound image data with the heartbeat of the patient. For example, a sequence of images may be associated with a sequence of ECG readings revealing the phases of the cardiac cycle, or images may be captured only at a specified phase of the cardiac cycle as explained below with respect to FIG. 9.

In some embodiments, the image display unit 70 can convert the ultrasound data generated by the beam-former 54 (which may be relative to a transducer-centered polar coordinate system) into an image relative to another set of coordinates, such as a rectangular coordinate system. Such processing may not be necessary in the display unit 70 if the conversion was already preformed in the ultrasound unit 40. Techniques for converting image data from one coordinate system into another are well-known in the field of mathematics and computer graphics.

Figure 2:
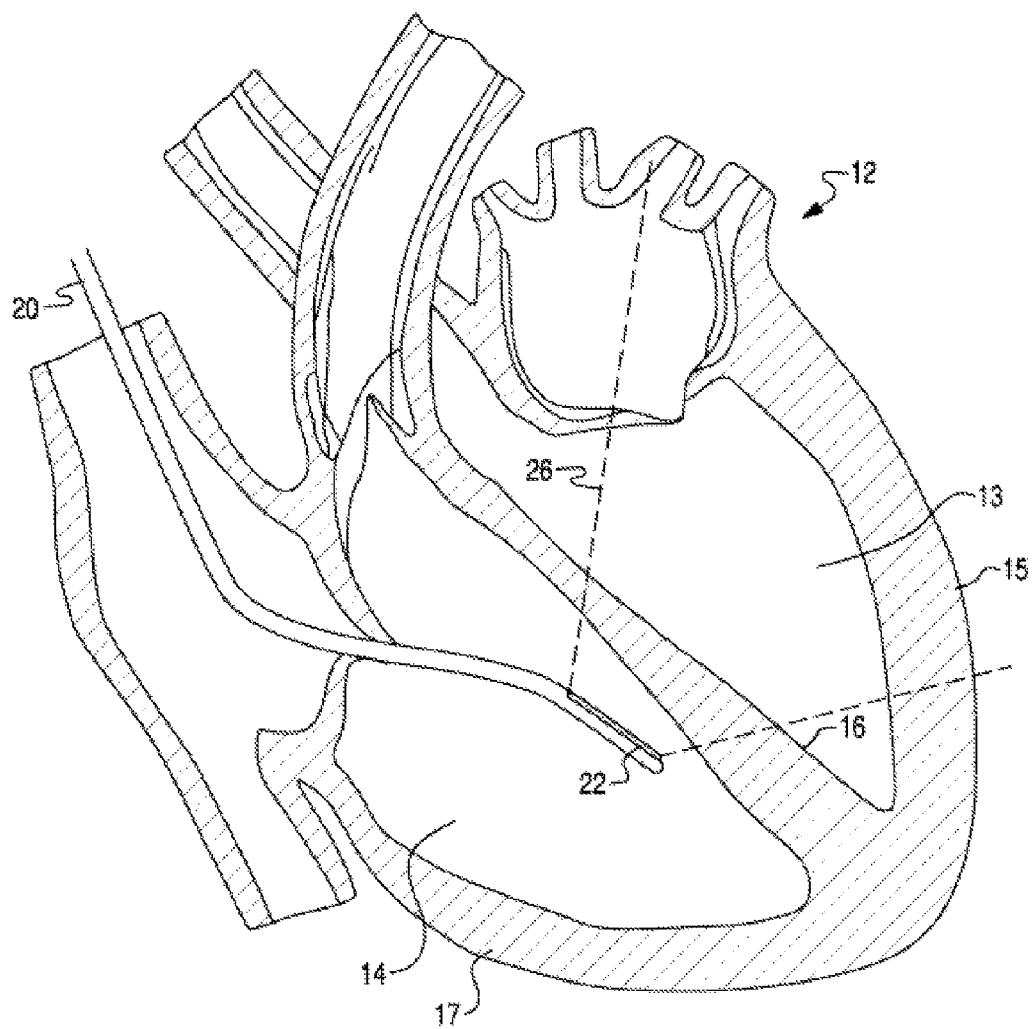
FIG. 2 is an illustration of an intra-cardiac ultrasound imaging catheter positioned in the right ventricular cavity.

FIG. 2 depicts a simplified cross section of a human heart 12 with an ultrasonic imaging catheter 20 positioned in the right ventricle 14. The catheter 20 includes an ultrasound transducer array 22, which can image at least a portion of the heart 12. For example, the image viewing angle 26 afforded by the transducer array 22 may allow imaging the left ventricle 13, the septum 16, the ventricular walls 15, 17, and other coronary structures from the right ventricle 14. Insertion of the catheter 20 into a circulatory system vessel or other anatomical cavity via percutaneous cannulation is well known in the medical arts.

Figure 3:
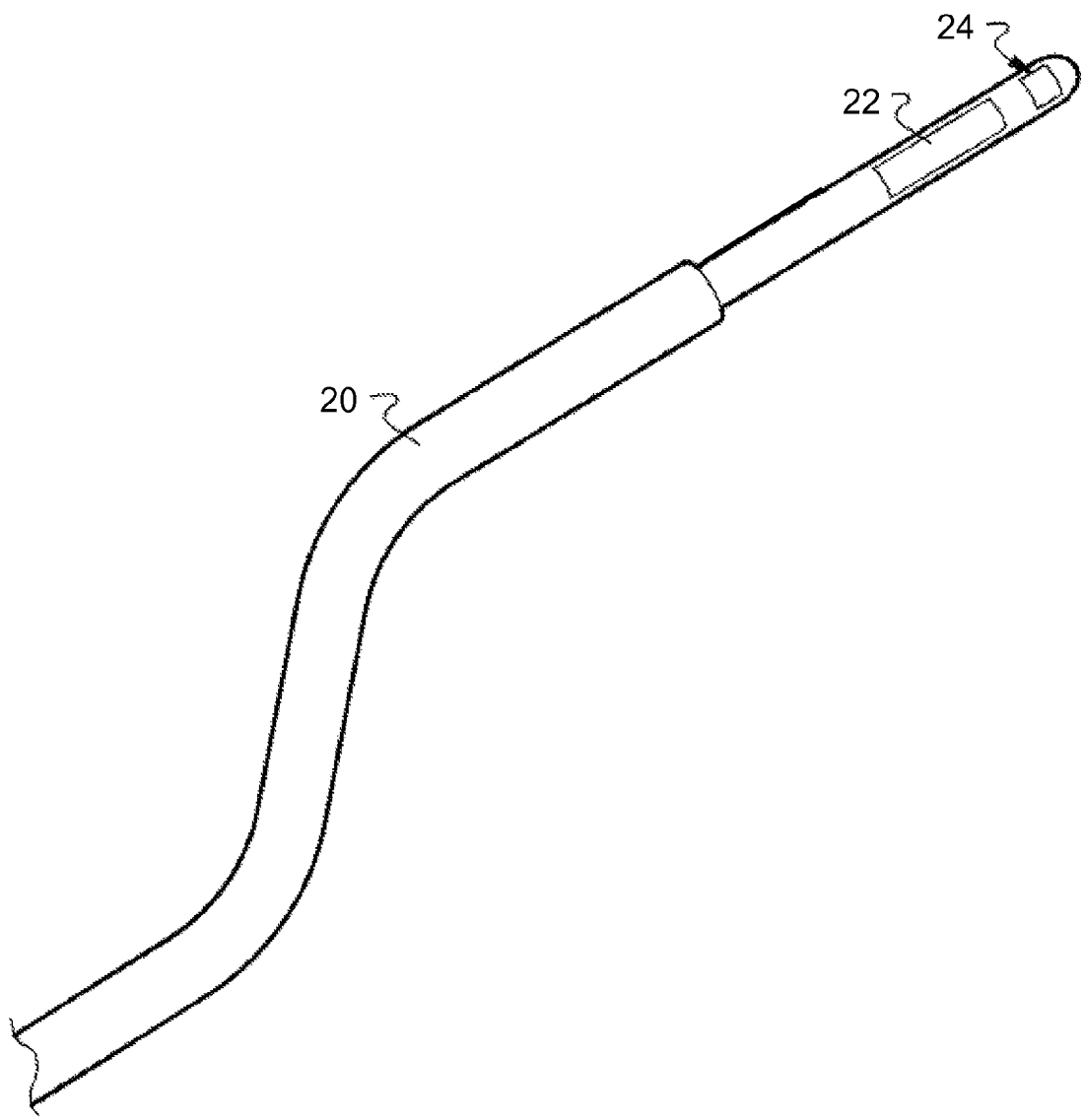
FIG. 3 is a diagram of an intracardiac ultrasound catheter with transducer array and temperature sensor.

FIG. 3 illustrates the distal end of a typical ultrasound imaging catheter 20. The transducer array 22 is typically positioned near the distal end of the catheter 20 behind a linear ultrasound window. Also, a temperature sensor, such as a thermistor 24, will be positioned in the catheter 20 near the transducer 22 and electronically coupled to a thermal monitoring circuit 42 to permit the system to cut off power to the ultrasound transducers if the measured temperature exceeds a safe limit. Examples of phased array ultrasound imaging catheters used in performing intracardiac echocardiography and methods of using such devices in cardiac diagnosis are disclosed in the following published U.S. patent applications—each of which is incorporated herein by reference in their entirety.

2004/0127798 to Dala-Krishna et al.;
2005/0228290 to Borovsky et al.; and
2005/0245822 to Dala-Krishna et al.

An example of a commercially available ultrasound catheter is the ViewFlex® available from EP MedSystems, Inc. of West Berlin, N.J. It should be noted that the present invention is not limited to the specific catheter assembly disclosed in the applications cited above, because the invention is applicable to various ultrasound imaging instruments designed for intravascular and intracardiac echocardiography.

The ultrasound echo return signals are radiofrequency signals that are typically converted to digital form and stored in memory 53. Memory used by an ultrasound imaging system may be a semiconductor random-access memory (RAM) or hard disc memory of the system or coupled to a network server. The beam-former 54 processes the returned echo signals received from the transducer elements to determine the time of arrival from which the distance to the source of each echo can be determined. Techniques for beam-forming for both transmission of the ultrasound pulse and reception of ultrasound echoes are well known in the fields of ultrasound imaging and in phased array ultrasound, sonar and radar.

The result of processing of the data stored in buffer memory 53 by the beam-former 54 can be a pixel-based image relative to a polar-coordinate system spanning the imaging angle. To generate such pixel-based image data, the amplitude, phase and time of arrival of reflected ultrasound pulses at each transducer in the array 22 are processed in the beam-former 54 to yield an RF signal reflecting the distance and intensity of echoes along the axis of the emitted beam, the angle of which (with respect to the long axis of the transducer array 22) is known. The distance and angle data may then be combined with amplitude (i.e., power of the received echo) to produce a pixel of image data (e.g., by processing the data according to an algorithm). Alternatively, the beam-former 54 may store or output the processed received ultrasound as datasets comprising data groups of angle, distance and amplitude. In this and like manner, the beam-former 54 can turn the large volume of streaming ultrasound signals into a smaller set of data easily passed over a data link 75 for processing or display by a display unit 70.

The beam former 54 may also compare the frequency of the generated signals with the frequency spectrum of the returned echo signals. The difference in frequency relates directly to the velocity of tissue or blood toward (higher frequency) or away from (lower frequency) the transducer array due to the Doppler Effect. The difference in frequency, i.e., the amount of Doppler frequency shift, is indicative of motion of the tissue (including blood) from which the ultrasound is reflected. The frequency shift may be determined by comparing the generated signal and received echo signal and detecting the difference in frequency. The conversion of the frequency shift to velocity depends on the speed of sound in the body, which is about 1450 to 1600 meters per second in soft tissue, including blood. The conversion of frequency shift to velocity according to well known algorithms may be performed immediately by the beam former 54, or later, such as by an external image processor at the time the image is displayed. If calculated by the beam-former 54, the velocity data (or Doppler shift) may be outputted as a fourth element of the dataset, so that echo sources are identified by angle, distance, amplitude and velocity (or frequency or Doppler shift).

The beam former 54 or the ultrasound unit 40 may directly produce an image in rectangular coordinates. Alternatively, the beam former 54 or the ultrasound unit 40 may produce an image in polar coordinates and transform the image into rectangular coordinates. Alternatively, the beam former 54 or the ultrasound unit 40 may simply produce an image in polar coordinates (i.e., angle and distance coordinates) and allow subsequent image processing to perform a coordinate transformation as needed (such as in image display unit 70).

A buffer memory 53 may make available the return signal data representing the ultrasound echo waves, and the beam-former 54 may access that data to calculate the amplitude of the ultrasound echo at each of many specific angles and distances from the transducer array.

A programmed microcontroller, microprocessor, or microcomputer 41 or functionally equivalent discrete electronics can be included to coordinate the activity described above within the ultrasound unit 40. In addition, the microcomputer 41 (or equivalent) may respond to configuration parameters and commands sent from the image display unit 70 over the communication interface 75 or 76 to the ultrasound unit 40. This microcomputer 41 within the ultrasound unit 40 may be in addition to a system processor, which is a programmable computer, such as a workstation or laptop computer, that is electronically coupled to the ultrasound unit 40. In such configurations, the microcomputer 41 may receive configuration and control instructions from the system processor which can have a user interface (e.g., display with menus, pointer device and keyboard). In some system configurations, the activities of the ultrasound unit 40 may be controlled directly by the system processor.

In an embodiment, the ultrasound unit 40 may be configured via software or discrete circuits to adaptively cut and separate each image frame of ultrasound image data. Such capability may be used to select and transmit frames for which there is useful information (e.g., changes in position of structures) to limit the bandwidth required for transmitting ultrasound images to external displays. In a normal cardiac cycle, portions of the heart are at rest for significant fractions of the cardiac cycle, so numerous images during such intra-contraction periods, illustrated as durations 600 in FIG. 6A, will contain the same image information. Alternatively, images may be selected during the intra-contraction periods 600 for processing since the relative stability simplifies image processing and combining of images. By not transmitting images from portions of the heart beat cycles, the desired image information may be transmitted at substantially lower data rates. Such processing of image frames may be accomplished by a segmentation module (not shown).

In an embodiment, signals from an ECG sensor such as an electrophysiology catheter 66 may be used in lieu of, or in addition to, signals from an external ECG unit 60, which may have its own ECG sensor or sensors. The ECG sensor signals can be used to record or control the timing of the ultrasound image acquisition relative to the cardiac cycle instead of or in conjunction with signals from an external ECG unit 60. The signals from an ECG sensor may be included within the data stream outputted by the ultrasound unit 40.

In addition to including connectors for receiving the input/output connection plugs for ultrasound catheters and ECG sensors or equipment, some embodiments of the ultrasound unit 40 include connections for additional sensors, such as intracardiac percutaneous leads, subcutaneous leads, reference leads and other electrical leads that may be employed during a procedure.

A scan converter 82 may be used reformat polar coordinate image data into an image relative to a rectangular coordinate system as needed. Image data from the scan conversion (and Doppler processing, if any) may be processed by an image renderer 83, then formatted and displayed as an image on a video monitor 73. For example, the rendering circuit 83 may generate a gray-scale image (such as a B-mode image) in which the brightness of each pixel is representative of the amplitude of the ultrasound echo from the anatomical small volume to which the pixel corresponds.

The image display unit 70 may perform other functions. For example, the interactive control 80 in the image display unit 70 may transmit configuration parameters and control commands to the ultrasound unit 40, where the configuration parameters and commands may be supplied by the operator by means of interactive inputs from a pointing device (mouse, trackball, finger pad, or joystick, for example) and a keypad or keyboard 72 attached to the display unit 70. Optionally, the interactive control 80 of the image display unit 70 may forward the image and/or raw data to a network file or database server, to the Internet, to a display screen, or to a workstation through a communication interface 92.

In an embodiment, the image display unit 70 circuitry may be included within the ultrasound unit 40 housing or chassis. This may be accomplished by simply including the image display unit 70 circuitry as another board or VLSI chip within the ultrasound unit 40. Alternatively, the circuitry and functionality of the components of the image display unit 70 may be incorporated in a VLSI chip that also encompasses the beam-former 54 and/or microcomputer 41 within the ultrasound unit 40. In such an embodiment, one or more of the various image processing method embodiments describe below may be programmed into and be performed by the image display unit 70 circuitry or a microprocessor within the ultrasound unit 40. In such an embodiment, the ultrasound unit 40 outputs the processed image data as a video signal (e.g., VGA, composite video, conventional television or high-definition video) that can be carried by a cable 75 directly to a display 73 to yield an image on the screen without further processing. In a further embodiment, the ultrasound unit 40 may output processed image data as a network compatible signal, such as Ethernet or WiFi, that can be directly coupled to a network.

One or more display monitors 73 may be included as part of ultrasound unit 40. Any of many choices, sizes, and styles of a display 73 may be connected to the ultrasound unit 40. For example, the external display monitor 73 may be a cathode ray tube, a liquid crystal display, a plasma display screen, "heads up" video goggles, a video projector, or any other graphical display device that may become available. The display monitor 73 may be large and may be located conveniently out of the way, such as a plasma screen hung from the ceiling or on a wall. The display monitor 73 may be positioned for better viewing by the physician, and may be positioned remotely, such as in another room or in a distant facility. The display 73 may be connected to the ultrasound unit 40 by a cable, an infrared link, a radio link (such as Bluetooth), or any equivalent wireless technology.

In an embodiment, the display monitor 73 and/or the user input device 72 may be embodied by a computer terminal, workstation, or personal computer such as a laptop computer. Such an embodiment can be configured to display the graphical output from the image rendering circuits 83 and to pass user inputs on to the interactive control 80 of the ultrasound unit 40. Alternatively, in an embodiment in which the display monitor 73 and user input device 72 are provided by a computer system, the computer system may operate software enabling it to perform one or more of the image processing method embodiments describe below on the data received from the ultrasound unit 40.

As useful as intra-organ ultrasound images can be to a clinician, the images obtainable from a catheter mounted ultrasound imaging system are necessarily limited to two dimensional slice (i.e., cross-sectional) image frames. This limitation to two-dimensional imaging results from dimensional limitations inherent in a catheter ultrasound imaging instrument. On the one hand, an imaging catheter must be less than about 10 French in size in order to safely access the interior of human organs, such as the heart. A catheter of a larger diameter could present insertion complications, clotting, and flow-blockage risks to the patient. Also, larger diameter catheters are more difficult to bend through the arteries or veins by which access to an organ is obtained. On the other hand, piezoelectric transducers are limited to a minimum size range by the ultrasound frequencies desired for imaging purposes. In the intracardiac imaging application, desired ultrasound frequencies range from 3 to 10 MHZ, and typically range between 5 and 7 MHZ. In order to be able to produce ultrasound within this frequency range, each transducer element must have a minimum dimension (length, width and height) of approximately 0.2 square millimeters Further, the spacing between such elements is also governed by the range of imaging frequencies employed, and the related side-lobe characteristics based on the lateral sensitivity of the crystal configurations used. For example, a linear phased array imaging at 4.5 MHz to 7.5 MHz, could have a pitch of 0.2 mm. As a result of these two dimensional limitations (i.e., catheter diameter and minimum transducer dimension), the only configuration possible for a phased array of piezoelectric transducers in an intracardiac catheter is a linear array aligned with the long axis of the catheter. A conventional intracardiac linear phased array ultrasound imaging catheter is shown in FIG. 3.

Figure 4:
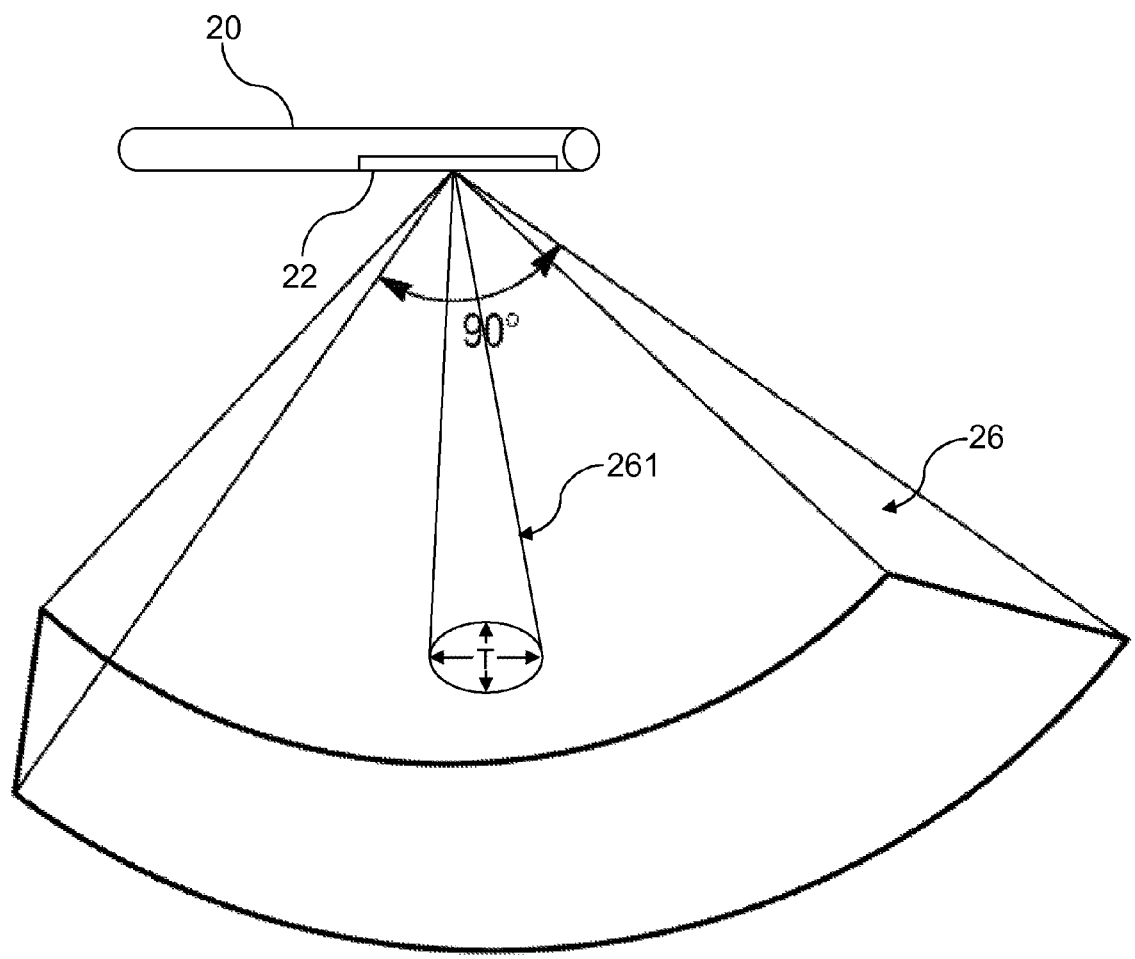
FIG. 4 is a diagram of the imaging area of an intracardiac ultrasound transducer array.

A linear phased array ultrasound transducer 22 can only generate a two dimensional slice image spanning an angle of imaging 26 by steering the ultrasound beam 260 up and down along (i.e., parallel to) the long axis of the array, as illustrated in FIG. 4. Consequently, a linear phased array ultrasound imaging catheter acquires a two-dimensional image with an image plane parallel to the long axis of the catheter. Since the emitted beam is not a pure line but a narrow conical beam (i.e., it has a diameter), the image plane has a thickness T depending upon the distance from the transducer. However, the ultrasound system records echoes as single returns with distance from the transducer 22 determined from the time of arrival of each echo. Each echo may be represented as a pixel on an ultrasound image frame. Due to the finite pulse width and the height and width of the beam T, each pixel in the ultrasound image frame represents a small volume. This volume is small as the typical intracardiac ultrasound transducer emits a beam of sound that has an angular dispersion of approximately 0.5 mm at typical imaging distances. For this reason ultrasound pixels are sometimes referred to herein as "voxels" consistent with the use of that term in the ultrasound imaging arts. Even though the resulting ultrasound image frame represents a thin volumetric slice, it is not a three-dimensional ultrasound image. To generate three-dimensional images, a number of generally contiguous ultrasound image frames must be combined, such as by using methods according to the various embodiments of the present invention.

For some diagnostic applications, it will be advantageous to generate three dimensional images in order to view significant portions of an organ at the same time. For example, in the heart, a two-dimensional image frame shows only a small cross-section of the heart at a time. Yet, the heart is a very complex three-dimensional structure. If the transducer array is oriented to view a cross section of the heart that contains healthy tissue, the clinician may not detect adjacent tissue which is behaving abnormally or is diseased. Further, as the heart beats, the surfaces of the ventricles and atria move in a complex fashion. Thus, it is difficult for a clinician to visualize the entire heart or comprehend how the various structures are moving throughout the cardiac cycle when the clinician is only able to view a single thin slice image at a time.

To overcome the limitations of this two-dimensional imaging capability, clinicians will typically rotate the catheter during an examination in order to view slice images of different parts of the heart. By rotating the catheter back and forth, a clinician can scan the inside of the heart, much like swinging a flashlight back and forth to view a dark room. While this procedure allows the clinician to see much of the heart, it is necessarily limiting in utility for at least three reasons. First, the clinician must rely upon memory to piece together the various views obtained in each of the two-dimensional slices in order to visualize the three-dimensional structure of the heart. This procedure may be facilitated in offline analysis when multiple adjacent images may be displayed on a computer screen simultaneously. However, such methods have limitations since it is difficult to visualize a three dimensional image of an organ with a shape as complex as the human heart. Also, the viewing perspective (i.e., position and orientation) of the imaging transducer may change from image to image as the catheter is rotated. Second, the heart is a dynamic organ, moving and changing shape several times per second. Consequently, as the ultrasound imaging transducer is rotated to a new viewing angle, it is imaging the heart at different instants in the cardiac cycle. The clinician may attempt to overcome this disadvantage by slowly rotating the catheter so that multiple beat cycle images are observed at each rotational orientation. However, this extends the examination procedure and further complicates the clinician's task by requiring visualization of the three dimensional structure which is changing shape constantly. Third, when the clinician rotates the catheter, the position and angular orientation of the transducer array may move in an unpredictable manner. For example, rotating the catheter may cause the transducer to shift laterally in position and/or rotate upward or downward with respect to the previous viewing orientation. Also, forces from movement of the heart or blood flow may cause the transducer array to move from image to image. Consequently, a clinician is unable to know whether changes in location of imaged structures viewed in subsequent two-dimensional slicing images are the result of the shape of the heart structure or movement of the transducer array with respect to the structure, or both.

As result of these difficulties, current intracardiac ultrasound catheter imaging systems have little if any ability to generate three-dimensional images of the heart. Methods for correlating ultrasound images in time, particularly with respect to the cardiac cycle, have been disclosed in U.S. Pat. No. 5,722,403 and U.S. Patent Publication No. 2005/0080336, which are both hereby incorporated by reference in their entirety. Nevertheless, additional methods are needed for accurately stitching together two-dimensional ultrasound images in order to render an accurate three-dimensional representation of cardiac structures. While cardiac imaging represents a particularly urgent need for image processing and combining methods, such methods could also be useful in the examination of other organs. To address this need, the various embodiments enable the generation of three-dimensional images and four-dimensional (i.e., three-dimensional plus time) movies (also referred to herein as "cines") from a series of two-dimensional ultrasound image frames. The embodiments also enable the generation of three- and four-dimensional image datasets to enable virtual close inspection of particular portions of the heart.

In order to generate such merged images from a dataset of ultrasound images, a number of technical challenges must be overcome. Before a sequence of images can be combined, the images need to be correlated in time (particularly for a moving organ like the heart) and with respect to the transducer viewing perspective (e.g., its position/orientation). Additionally, the inherent variability in ultrasound image quality from frame to frame due to noise, speckle and other phenomena needs to be processed out or otherwise accounted for. Finally, the raw two-dimensional images or the assembled three-dimensional image may need to be processed to identify or emphasize clinically significant details or features. These and other technical problems are addressed in the various image processing embodiments described herein.

To obtain a series of two-dimensional ultrasound image frames using a system like that illustrated in FIG. 1, a sterile ultrasound imaging catheter 20 may be introduced into the patient's body, such as by percutaneous cannulation, and positioned so the transducer array 28 is at a desired location and orientation, such as guided by use of fluoroscopy. The ultrasound unit 40 is initialized and images obtained. The position and orientation of the imaging transducer array may be determined with respect to a frame of reference. The frame of reference may be with respect to the patient or the organ being imaged, with respect to the examining table, with respect to the examining room, or with respect to an arbitrary frame of reference, such as that of the fluoroscopy equipment or the examining table. Locating the imaging transducer within a frame of reference facilitates combining two-dimensional image frames obtained from the transducer by providing a known location (i.e., the source) in each image. Apparatus, systems and methods for locating the ultrasound imaging transducer within a patient are disclosed in U.S. patent application Ser. No. 11/610,357 entitled "Catheter Position Tracking for Intracardiac Catheters" filed Dec. 13, 2006, and Ser. No. 11/610,386 entitled "Catheter Position Tracking Methods Using Fluoroscopy and Rotational Sensors" filed Dec. 13, 2006, both of which are incorporated herein by reference in their entirety. It is noted that the step of determining the transducer position and orientation is not required for all embodiment methods, since some methods are able to align and co-register images by recognizing common structure points.

With the ultrasound system setup and configured, and the location and orientation of the imaging transducer array determined and recorded, a series of ultrasound image frames are obtained and recorded in the system. ECG signals may be recorded and stored in the system with the image data, such as in a correlated dataset. Once a sufficient number of two-dimensional images are obtained at a particular position and orientation, the transducer array can be rotated (and/or moved) to a new viewing perspective and the process of determining/recording the transducer position and orientation, obtaining/recording images and (optionally) recording ECG signals is repeated. Then, this process is repeated over a number of viewing perspectives in order to obtain a series of image frames spanning the region of the organ for which a three- or four-dimensional image or image database is desired.

Once the dataset of images, transducer locations and (optionally) ECG signals have been obtained, the image processing methods described below may be employed. These methods may be performed offline (i.e., after the images have been obtained) or in near real-time, (i.e., at the same time images are obtained), or a combination of in real time and offline processing.

In concept, assembling a series of ultrasound images into a three-dimensional image sounds easy; however, several technical challenges must be overcome to generate diagnostically useful three- and four-dimensional images from two-dimensional ultrasound image frames obtained from ultrasound imaging catheters. This is particularly true when the images are of the heart, and even more the case when the heart is diseased in which tissues may exhibit irregular, unpredictable movement, such as may occur during fibrillation.

The technical challenges which must be overcome to generate diagnostically useful three- and four-dimensional images from two-dimensional ultrasound images may be grouped in four categories. First, there is the challenge of determining the precise viewing perspective of the imaging transducer. In a beating heart deep within a patient, it is difficult to determine exactly from where an image was obtained, which makes it difficult to determine how images should be pieced together. Second, there is the challenge of imaging structure which is constantly in motion in order to assemble an accurate image of the structure at a particular dynamic state. This is particularly a challenge when the organ is moving in a random or unpredictable manner, as may be the case in a diseased heart. Third, ultrasound imaging presents unique image processing challenges due distortions and noise inherent in the nature of ultrasound, how it interacts with tissue and blood, and how ultrasound echoes are processed into images. Fourth, in order to use the three-dimensional images for precision diagnostic, treatment and surgical applications, imaged structure must be precisely located within a coordinate frame of reference useful for a medical procedure.

Determining the Imaging Perspective. Turning to the first technical challenge, an ultrasound imaging system must be able to identify the viewing perspective of each image in order to accurately assemble adjacent images. Without this information, it is not possible to distinguish a shift in viewing perspective from a curvature of structure between adjacent image slices. While this challenge is present in all situations where multiple images are combined into a composite three-dimensional image, within a beating heart the challenge is particularly difficult. This is due in large part to the fact that the ultrasound transducer catheter introduced into the heart via venal cannulation lies deep within the patient and far from the point of insertion. It is not possible to know the location and orientation of the imaging transducer array on the tip of the catheter by observing the location and orientation of the catheter handle. Additionally, the large volume of the heart chambers makes it difficult to identify the precise location of the transducer within a chamber (e.g., atrium, ventricle or vena cava). Further, the large volume of heart chambers permits the transducer tip to assume a wide range of orientations (i.e., it is not constrained to a particular orientation as would be the case of a transducer within a narrow vein or artery). Also, the rapid contractions of heart muscle and surges of blood through chambers and flow channels may cause the transducer end of the catheter to move unpredictably.

Figure 5:
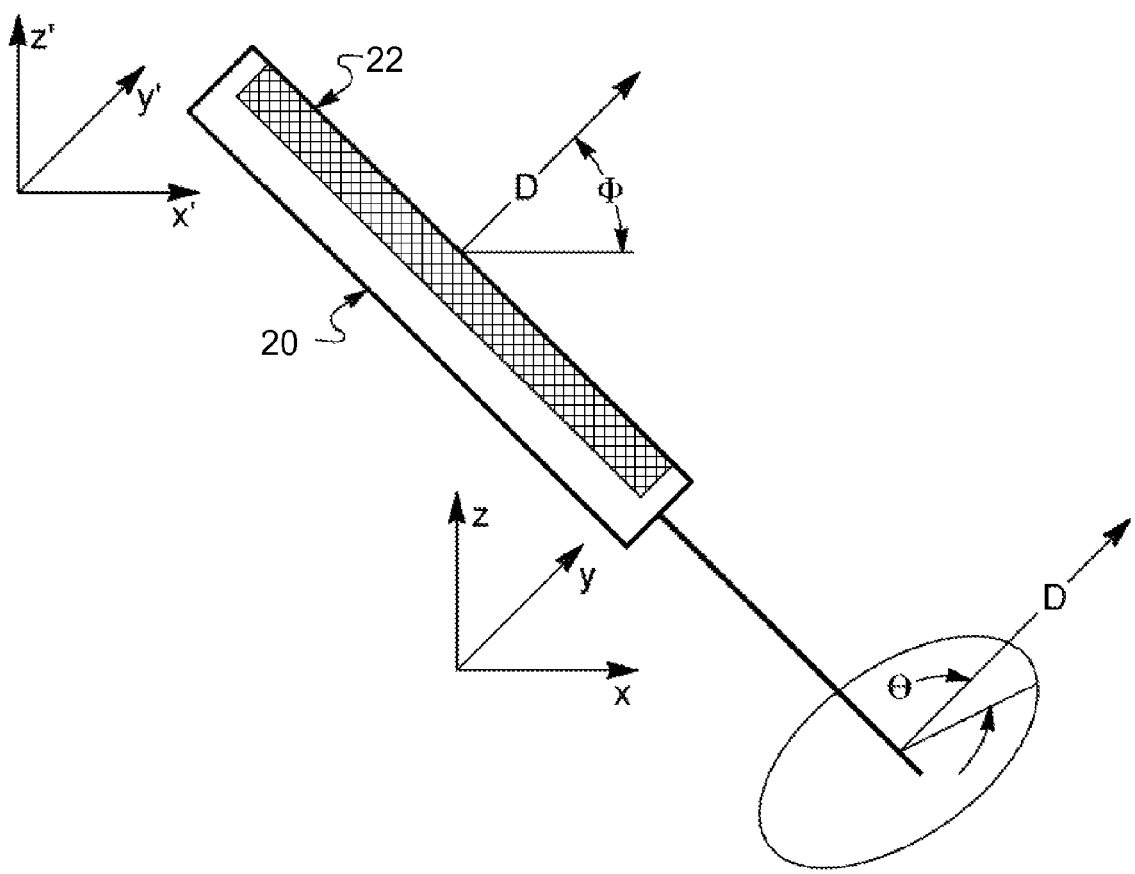
FIG. 5 is a diagram of an intracardiac ultrasound transducer array showing its positional and orientational degrees of freedom.

To accurately locate an ultrasound transducer within an organ of a patient in order to generate composite ultrasound images, both the location of the transducer in three-dimensional space and the transducer's orientation within three degrees of freedom (i.e., pitch, roll and yaw) must be known. As it is used herein, "position" generally refers to the location of at least one a point on the transducer array in three dimensional space, and "orientation" refers to the pitch, yaw and roll (i.e., rotation about the long axis) orientations of the transducer array about those three degrees of freedom. The location and orientation degrees of freedom are illustrated in FIG. 5. Referring to FIG. 5, the direction D represents the mid-line of the two-dimensional imaging plane (shown in the plane of the image) which extends along a plane parallel to the length of the array 22 and perpendicular to the face of the sound emitting faces of the array elements. As shown, the transducer tip is capable of being located in 3 dimensional space (represented by x', y', z'). Similarly, the base of the transducer can also be located in space through x, y, z dimensions. Further, the transducer can rotated through an angle of θ around its longitudinal axis and oriented so the linear array is tilted up/down (inclination or pitch angle) and angled left/right or into/out of the page (yaw angle).

The position/orientation of the transducer array 22 in each of these six degrees of freedom needs to be accounted for in constructing and combining images. Movement of the transducer array between one ultrasound image and the next through any one of the six degrees of freedom will result in significant changes in the viewing perspective. Thus, the positional measuring technique used with the ultrasound imaging system must fix the transducer's location in all six degrees of freedom (i.e., determine the values for the X,Y,Z dimensions and three orientation angles) within a short measurement time constant (i.e., minimum time to measure a position) relative to the contraction time of the heart.

Just as constructing three-dimensional images from a series of two-dimensional images requires knowledge of the transducer array position and orientation information for the six degrees of freedom, positional errors must be accounted for in each of these six dimensions. Errors in each dimension of position and orientation combine to yield the total positional error of each ultrasound image. Further, a combined image will have positional errors of features that are combinations of those of the component images. If the resulting total positional error of the series of ultrasound image frames is too large, the combination of the images will be fuzzy, unreliable or otherwise unusable for diagnostic purposes.

Such errors result from both the sensitivity of the position sensing mechanism used and the cumulative integration and derivation errors involved in position/orientation calculations.

Imaging and processing images of a moving organ. Generating an accurate three-dimensional image of the heart is especially difficult because the organ is constantly in motion. Beyond the difficulties of determining the imaging perspective discussed above, a particular two-dimensional slice image shows the shape of the heart at only a brief instant in time. In the next instant, the heart will have changed shape so the next image may show heart structure in a very different configuration. To build up a three-dimensional image of the heart using two-dimensional slice images, the composite may be based on images taken when the heart is in the same shape. When the heart is beating normally in rhythmic fashion, its shape changes in a repeating pattern which can be used to select two-dimensional slice images that can be combined to generate an accurate three-dimensional composite image. Also, for diagnostic purposes, it may be most desirable to obtain three-dimensional images of the heart at many different phases within the heartbeat cycle, or a three-dimensional movie (referred to herein as a four-dimensional representation) of an entire cardiac cycle. Obtaining such three- and four-dimensional images from two-dimensional slice images taken over a span of time requires a large amount of image processing.

A rapidly moving heart poses a challenge related to correlating ultrasound images in time due to the duration of each ultrasound image scan and movement of the muscle between the images. Heart muscle may move rapidly during the peak of contraction, such as during the QRS complex portion of the ECG, illustrated in FIG. 6A, or during periods of fibrillation, illustrated as region 601 in FIG. 6B. Due to physical limitations, such as the speed of sound in blood, pulse repetition rate of the transducer, and the size of the heart itself, each two-dimensional ultrasound image frame takes a minimum amount of time to accomplish. If two images are taken during a period of rapid movement of heart muscle (such as during region 601 in FIG. 6B), the muscle may move a measurable amount between the two ultrasound image frames. The result may be a blurring or apparent thickening of the moving structure if the two image frames are added, averaged or otherwise combined. In situations of rapid heart movement, such as may occur in a diseased heart exhibiting fibrillation, the difference in the time of the portion of the image at the beginning of an image scan to the end of the image scan may be significant.

As explained above, the linear phased array transducer generates a two-dimensional slice image by steering a series of millisecond ultrasound pulse beams through a series of angles with respect to the transducer array face, e.g., from −45 degrees to +45 degrees to the perpendicular. This scanning of the ultrasound beam is illustrated in FIG. 4. In a typical intracardiac linear phased array transducer system, each scan from the bottom of the image to the top spans approximately one-sixteenth ($\frac{1}{16}$) of a second. For these reasons, careful consideration needs to be given to how ultrasound images are identified in time ("time stamp") and the inherent error associated with such time values. For example, the time stamp of an image may be assigned when the imaging scan begins (i.e., when the first pulse is generated), in the middle of the imaging scan (i.e., when the ultrasound pulse is directed perpendicular to the transducer array), at the end of the imaging scan (i.e., after the last echo of the last scan pulse is received), or at some point in between.

In addition to addressing the finite duration of each ultrasound image frame, image processing must recognize and accommodate the fact that different parts of the image, such as the outer edges of the image will have larger time value errors (i.e., errors in the time value assigned to each portion of an image) than other portions of the image. In ultrasound imaging, a pixel time error is directly proportional to pixel position error (related by the speed of sound in blood and tissue). Therefore, such time errors can become significant when assembling a composite image of heart structure from many ultrasound images.

In addition to these image time errors inherent in each two-dimensional image frame, consideration must be given to timing errors introduced by the use of ECG signals to correlate cardiac images. While the heart follows a rhythmic and repeating pattern in response to electrical signals picked up by ECG electrodes, there is some inherent variability beat-to-beat, both in the timing of contractions against the ECG signal and in the movement of individual portions of the heart. In a diseased heart, the heart muscle coordination with the ECG signal is poor, particularly in the atrium where electrical signals may not match the tissue motion. As a consequence, if the ECG signal is used to correlate or time-gate two-dimensional slice images in order to build up an image set showing a three-dimensional portion of the heart, the correlation method must recognize and accommodate the timing and positional errors due to (1) differences between the heart's electrical activity and mechanical movements, (2) the finite duration of each imaging scan, and (3) the round trip duration of individual ultrasound pulses.

Consideration should also be given to the relationship between the speed of anatomical structure movement and the sensitivity of the ultrasound image. When heart muscle walls are moving rapidly with respect to the imaging duration (i.e., the amount of time required to acquire a single two-dimensional ultrasound image frame), the result may not yield a "bright" image of the moving structure. For example, if the ultrasound imaging pulse has a pulse width $\Delta T$ (which is typically about $\frac{1}{65}^{th}$ of a second), the associated image may be recorded as occurring at T1, T1+ΔT, or any time in between. If the atrial wall being imaged is moving rapidly, its position at T1 may be removed from its position at T1+ΔT, and the resulting image may be blurred so that it is difficult to identify edges or accurately measure the position of the vessel wall. Also, a moving structure will appear tilted as the structure moves during the time the transducer array scans from the bottom of the image sector to the top. Such blurring and distortion of moving structure may need to be considered in edge recognition algorithms used to recognize structure in ultrasound images.

Challenges inherent with processing ultrasound images: Generating an accurate three-dimensional image of the heart from two-dimensional ultrasound slice images also requires solving a number of problems caused by or inherent to two-dimensional phased array ultrasound imaging. These problems include: distance-dependent "voxel" volume; signal attenuation with imaging distance; image noise and "speckle;" and multipath sound scattering creating pseudo-edges.

Distance-dependent Voxel Volume. Any image processing method which combines multiple images or recognizes structures using edge recognition techniques should account for the fact that the volume represented by each "voxel" of information depends upon the distance from the transducer array. This is due to the geometry of a phased array scan, wherein the center of the transducer forms the source point of each scan line, from which an evenly disperse angularly displaced set of scan lines form the scanned image. Thus, the distance between any two scan lines increases as a function of distance from the surface of the transducer. This can further be extended to any rotational image acquisition, where individual image slices, angularly displaced from a common origin point (the center of the transducer), move further apart with distance from the scan origin. The angle of resolution of the transducer array depends upon the length of the array, the wavelength of the ultrasound pulse, and the angular sensitivity. A typical intracardiac transducer array is approximately 13 mm long and the ultrasound wavelength is approximate 0.3 mm in blood. The volume represented by a pixel, i.e., a "voxel", of ultrasound information increases with distance from the transducer array. For example, in a typical intracardiac ultrasound imaging application, the volume of an image voxel at a typical maximum imaging depth of 16 cm is 60% greater than the volume of an image pixel at the typical minimum imaging depth of 10 cm.

This distance-dependent voxel volume relationship can result in image distortion when various two-dimensional images are combined into a three-dimensional composite image. Also, if images of structure taken from different imaging depths are combined, the structure images will need processing to take into account the different volumetric resolutions of pixels in the respective images. Further, imaging processing methods which rely upon edge recognition algorithms may need to account for imaging distance in order to have consistent edge resolving capabilities over the entire image.

Signal Attenuation. Attenuation of ultrasound in tissue and blood limits the imaging depth achievable with the ultrasound frequencies and power level used in intracardiac imaging. As it passes through tissue, ultrasound is scattered and absorbed by tissue and blood, reducing the amount of energy returning to the transducer array. Consequently, the amount of ultrasound returning to the transducers from structure at the far edge of the ultrasound image will be much lower than from structure closer to the transducer array. As a result, there will by a lower signal-to-noise ratio in image pixels near the edge of the imaging depth than closer to the transducer array, and thus lower imaging sensitivity. Image processing methods which do not take this phenomenon into account may not recognize structure near the maximum imaging depth, or may interpret noise as structure. Also, structures near the maximum imaging depth may appear ill-defined or insubstantial due to signal attenuation even though the structure is thick (e.g., a ventricular wall). If the gain on received ultrasound is increased in order to identify structure near the maximum imaging depth, the result may be increased noise in the near field portion of the image.

Image Noise and "Speckle". In addition to the foregoing image processing challenges, an ultrasound imaging system must also deal with noise in ultrasound image frames. Three sources of noise in ultrasound images should be accounted for. First, electronic noise is caused by ambient electromagnetic interference (EMI). A typical "cath lab" has numerous EMI emitters in the form of electronic equipment, computers, fluoroscopy equipment, power and lighting sources. EMI noise can be significant because the electrical signals received from ultrasound transducers are very weak and must be amplified significantly to generate an image.

The second source of noise in ultrasound images are due to random or enhanced echoes of ultrasound pulses which can appear as random pixels and bright spots, referred to as speckle. Some specular reflections are caused by constructive interference of sound waves reflected off of closely spaced structure layers (such as cell layers separated by about one-half the ultrasound wavelength). Such structure-related speckle can be used for locating and tracking structure, such as disclosed in U.S. patent application Ser. No. 11/610,888, entitled "Method And System For Estimating Cardiac Ejection Volume And Placing Pacemaker Electrodes Using Speckle Tracking," which is hereby incorporated by reference in its entirety. Other sources of speckle are random in nature, appearing as light pixels in one image that are not present in the next.

Figure 7:
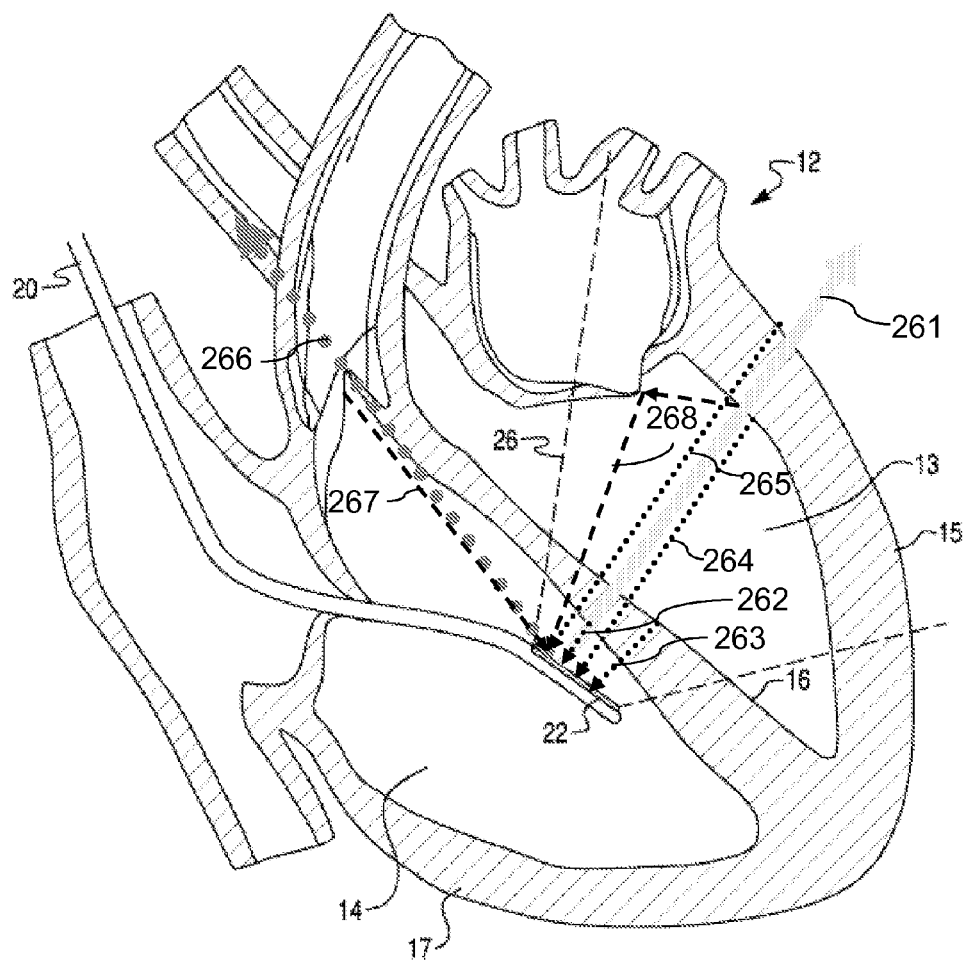
FIG. 7 is an illustration of an intra-cardiac ultrasound imaging catheter positioned in the right ventricular cavity illustrating the phenomenon of multipath interference.

A third source of noise in intracardiac ultrasound images is caused by echoes from ultrasound beam side lobes and ultrasound scattering off of multiple structures and blood such that sound follows an indirect path before returning to the transducer array. Referred to herein as "multipath" scattering, such sound waves approach the transducer array from an angle different from the original ultrasound pulse and may arrive delayed in time due to the longer path that the sound traveled. As illustrated in FIG. 7, one source of multipath scattering is caused by ultrasound from the main beam 261 being refracted and/or scattered by tissue and blood so that it follows indirect paths 268 back to the transducer 22, unlike normal ultrasound echoes which follow direct paths 262, 263, 264, 265 back to the transducer 22. Since ultrasound following an indirect path 268 travels further before returning to the transducer, the ultrasound system may interpret multipath sound as being reflected from more distant structure. Additional multipath interference can arise from echoes of beam side lobes 266. While the linear phased array transducer generates a focused primary beam 261, some of the ultrasound energy is emitted at an angle to the primary beam in the form of side lobes 266. Echoes 267 of side lobe ultrasound from structure will return to the transducer, and may be interpreted as being reflected from structure along the axis of the primary beam 261. Multipath sound scattering thus can be a source of noise and false signals in ultrasound images.

Correlating ultrasound images to a usable frame of reference. For many diagnostic purposes it is important to correlate the ultrasound image to a frame of reference so that the position of imaged structure can be located with respect to the patient's body, the examining table, other examination or surgical equipment or another frame of reference. For example, telerobotic, image guided or arthroscopic surgical or therapy systems are capable of positioning a surgical or therapy instrument at a precise point within a patient. To guide such equipment to a particular point for a procedure, the ultrasound image results need to be correlated (registered) to the positioning frame of reference of the surgical or therapy equipment. As discussed above, the position of the intracardiac ultrasound image transducer within the patient is difficult to determine. This challenge is magnified when the ultrasound images must be precisely located within an external coordinate frame of reference of a precise machine-guided instrument system.

The foregoing imaging and image processing challenges may be overcome using one or more of the following image generation and image processing method embodiments.

Determining the transducer position/orientation. A number of methods for precisely locating a catheter within a patient have been proposed and developed. Example methods and equipment for such purposes are disclosed in U.S. Pat. Nos. 5,515,853 and 6,192,266. Additional example methods and equipment for such purposes are disclosed in the following U.S. patent application Ser. No. 10/994,424, published as US 2006-0122514 A1, entitled "Method And Apparatus For Localizing An Ultrasound Catheter;" Ser. No. 11/610,357, filed Dec. 13, 2006, entitled "Catheter Position Tracking for Intracardiac Catheters;" and Ser. No. 11/610,386, filed Dec. 13, 2006, entitled "Catheter Position Tracking Methods Using Fluoroscopy and Rotation Sensors." Each of the aforementioned patents and patent applications are incorporated herein by reference in their entirety.

The frequency of baseline transducer position measurements and rotational position estimations (using any of the techniques described in the foregoing U.S. patent applications incorporated by reference) as well as the imaging frame rate need to be sufficiently high to provide the degree of resolution required by the particular diagnostic objective. Further, the positional (baseline measurements plus instantaneous displacement estimates) and rotational measurements and imaging scans may need to be timed so that all three of these measurements/estimations occur within an acceptable time-span or time-correlation error band to permit clinically acceptable three-dimensional image generation. This latter concern may arise because the duration required for recording each position/orientation measurement and/or image scan may be different. As a result, there will be errors (i.e., degree of uncertainty) in the time at which each position measurement is obtained and thus a position/orientation error associated with each ultrasound image. If such errors are not properly managed or otherwise taken into account during image processing, the result may be a blurring of the generated three-dimensional images.

Figure 8:
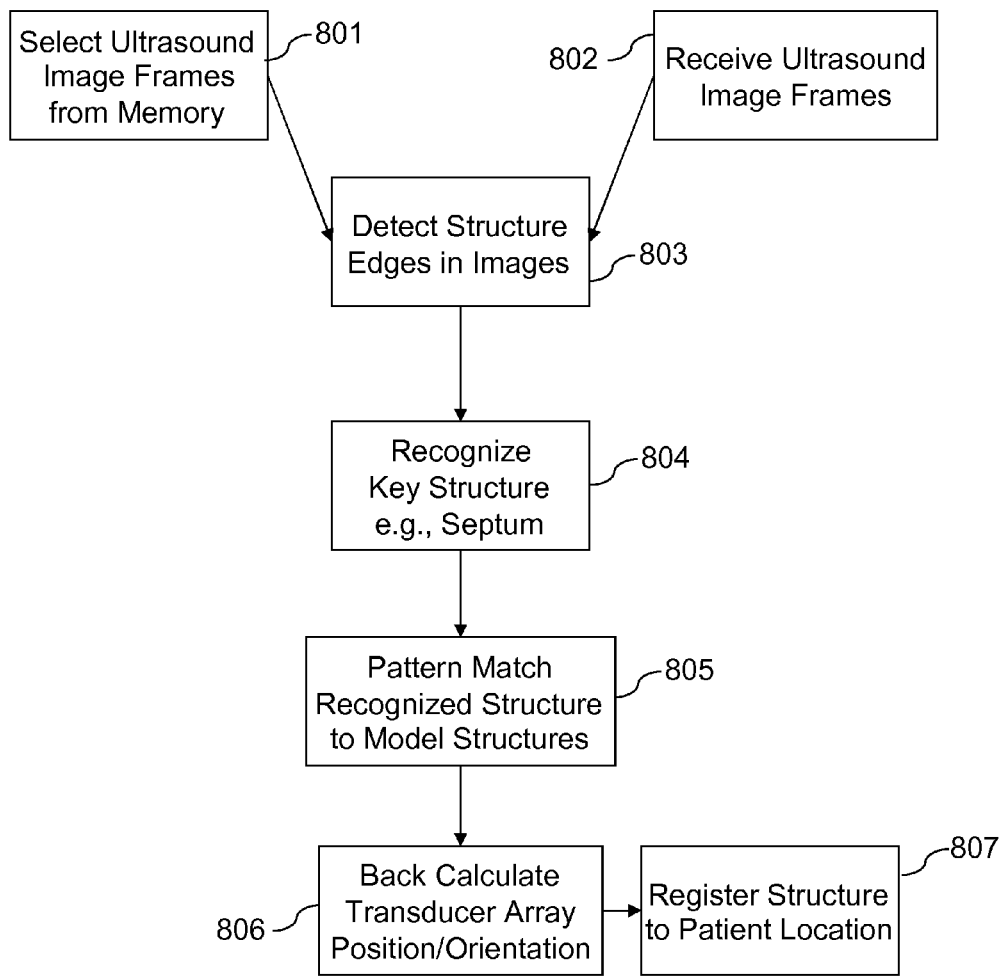
FIG. 8 is a flow diagram of an embodiment method for determining the transducer position and orientation by processing ultrasound images.

In an embodiment illustrated in FIG. 8, the limitations and errors of measuring the transducer position and orientation by external means are obviated by processing the obtained images to estimate the transducer orientation from the images themselves. In this embodiment, image frames are processed to determine the position and orientation of the transducer array with respect to known or recognized structures in the image. Ultrasound image frames may be accessed from memory, step 801, or received directly from the ultrasound imaging system step 802. Images from either source are processed using edge-detecting image processing algorithms, step 803, to recognize the surfaces of structures within the heart and store positional information for the recognized surfaces.

Edge-detecting algorithms determine the edge of a tissue structure by noting a sudden rise (for leading edge) or fall (for trailing edge) in brightness across a short distance. Heart tissue structures may not exhibit a single bright edge in ultrasound, and instead exhibit a reflectivity gradient across the endothelial layer and other tissue layers between the outer edge and the inner portion of the structure. As a result, determining where the structure edge lies may require image processing using a number of alternative or complementary algorithms to decide where a structure edge exists or where the edge should be determined. For example, for some structures, the processor may compare the brightness (i.e., amount of reflected ultrasound) versus distance along each ultrasound beam to detect a sudden rise over a short distance (e.g., large $\Delta$brightness/$\Delta$distance) and determine that an edge exists at a pixel where this rate of change exceeds a threshold.

As another example, which may be used alternatively or in addition to the first example, the processor may first determine that a structure exists in a portion of an image frame and then determine the edge of that structure. In this second example method, the processor may first recognize that a structure exists along a portion by noting that the portion has a higher average brightness than other darker portions where there is no structure (i.e., the darker portions contain blood which reflects less ultrasound). Once a structure has been recognized, the processor can compare brightness values of pixels along a line segment spanning the determined structure and a portion of the darker region to determine where the edge of the structure exists. This determination may be based upon a number of criteria, such as for example: (a) a point of inflexion of the brightness versus distance along this line segment, (b) a pixel with an intermediate brightness value (such as the pixel closest to the median brightness value, or the pixel having a brightness value that is some fraction of the difference between the average bright and average dark region pixels) between the darker region and the brighter region, (c) the first pixel in the segment with an increased brightness over the darker region, or (d) the first pixel in the segment that has brightness value approximately equal to or greater than the average brightness in the bright region. These four example criteria will set the edge of the structure close to the outer portion of the structure (the true edge), toward the middle of the edge region, or at the inner edge where the structure's inner tissue begins.

Other decisional criteria may also be employed, such as an iterative and statistical analysis of all edge regions in the image frame to selected a criterion that provides a smooth (i.e., non-discontinuous) edge across all radians in the image frame.

When the processor recognizes that a structure exists at a particular location, the image data can be stored as the positional (X, Y, Z) measurements of the edge location (e.g., as a three-dimensional vector), rather than as image pixel data. This process can thus generate a three-dimensional structure surface dataset. When the back edge is determined by the processor and the positional measurements stored as another structure surface dataset, the area between the inner and outer surfaces defines the area of the structure in the cross sectional image. The processor may thus define and store a volumetric structure dataset.

With recognized surface and structure datasets from each image frame stored in memory, the processor then can measure the distance and angle to the recognized structure, as well as structural dimensions, and from such measurements deduce the location of the transducer at the time the ultrasound image frame was obtained, step 804. Recognizing the structure and using the process to determine the imaging perspective may be best accomplished using easily recognized structure which undergoes little movement during the cardiac cycle. For example, the septum is generally planar and remains in a relatively stable position with respect to the rest of the heart during the cardiac cycle. Also, the septum is thick compared to other heart structures, and thus may be recognized by the processor based upon the distance between the inner and outer edges compared to a table or range of typical septum thickness values or compared to other heart structures in the image. Also, in certain viewing positions, such as when the transducer is in the right ventricle oriented toward the left ventricle as shown in FIG. 2, the septum may be recognized as being the closest structure to the transducer. The septum may also be imaged using fluoroscopy (albeit faintly) in order to provide localizing information using an external sensor. In many ultrasound viewing perspectives used in cardiac diagnostic procedures, the septum will be included (at least partially) within the ultrasound image, and therefore useful as a common reference structure within two dimensional ultrasound image frames. Other useful structures that may be recognized by the processor for the purpose of self registration of ultrasound images include portions of the bicuspid and mitral valves and the interior surfaces of the ventricles.

Once the heart structure has been recognized and its surface and/or volumetric datasets determined, the processor can compare this information to an anatomical model of the heart, step 805. Any of a number of known algorithms for comparing measured dimensions to three-dimensional digital models may be used to conduct this comparison. Then, using the comparison, the processor can back calculate from this comparison to estimate the location and orientation of the transducer that would yield the obtained image of the recognized structure at the measured distance and orientation, step 806. Any of a number of known algorithms may be used to estimate the transducer viewing perspective in this manner. The estimated transducer array position and orientation information may then be stored in memory with the ultrasound image frame for further processing, such as the generation of three-dimensional images.

Additionally, the measured position of recognized structure or the estimated transducer array position and orientation information can be correlated to an external frame of reference so the image data can be correlated to the patient's body, step 807. Any of a number of methods may be used to correlate the imaged structure or transducer array positional information to an external reference frame. For example, the transducer array may be imaged with fluoroscopy thereby providing a direct measurement of the transducer array in the two coordinate frames of reference. Similarly, the septum may be recognized and located in both fluoroscopy (in the external reference frame) and the ultrasound image surface or volumetric datasets (in the internal reference frame). Once a structure or the transducer has been located in the two reference frames, the processor can compute a coordinate transformation that will correlate the rest of the ultrasound image to the external reference frame.

Self registration methods may also make use of catheter position or orientation information which is not expected to change with movements of the heart. For example, the angular rotation of the transducer array about its long axis is unlikely to be affected by muscular contractions or blood flow around the catheter. Therefore, the rotational angle of the transducer array measured by a variety of methods (see, e.g., U.S. patent application Ser. Nos. 11/610,357 and 11/610,386 previously incorporated by reference) which may be combined with the self registration information obtained by recognizing a selected heart structure (e.g., the septum) to provide a more accurate estimation of the viewing perspective. For example, the septum will appear as a thick line in a two dimensional ultrasound image slice when the left ventricle is imaged from a position within the right ventricle. While the linear image of the septum will provide distance and angular information that can be used to estimate the transducer's distance from the septum, there may be ambiguity as to which part (edge, middle, top or bottom) of the septum is being imaged. By knowing the angular rotation of the transducer array, the processor can better estimate which portion of the septum is being imaged.

Self registration techniques can also use operator inputs, such as user designation of portions of the ultrasound image to select and identify structure to be used for registration purposes. Further, self registration techniques may use shape recognition algorithms to automatically recognize structures based on their shape, size, sonic characteristics, or other measurable characteristics.

In a user-designated structure embodiment, a clinician can point to a particular structure within a displayed ultrasound image, such as by using a pointing device like a mouse or light pen, to select and designate a particular portion of the ultrasound image to be used for image registration purposes. For example, the clinician may indicate the septum within an ultrasound image such as by touching the corresponding portion of the image with a light sensitive pen, or clicking a mouse button when the cursor is positioned on the selected structure. Once the structure has been selected, the clinician can then inform the processor, such as by means of a keyboard entry, that the designated structure should be recognized and used for purposes of aligning ultrasound images using self registration. The clinician may also identify the selected structure by a keyboard entry of information so the processor can look up that structure by name in the three-dimensional model of the heart. With this information, the processor can use edge recognition techniques to locate the same structure in other ultrasound images in the image database or received subsequently from the ultrasound system. This method allows the clinician to select structures which are likely to be present in all images to be obtained, relatively stable in all images and have a known or measurable position with respect to the portion of the heart being examined. For example, the clinician may select the septum for this purpose because its position relative to an imaged ventricle is known.

In the embodiment employing shape recognition to select structures for use in self registration of images, the processor can be programmed with digital three-dimensional anatomical models of an average heart. The processor then can be programmed to compare recognized structures (i.e., structures identified within an ultrasound such as by edge recognition algorithms) to the stored anatomical models in order to determine if there is a near match to a particular structure model. If there is a match, the processor then can use the anatomical model to estimate the location and orientation of the transducer array by working backward from the model using the position and orientation of the recognized structure within the ultrasound image. In this process embodiment, the processor may first process an ultrasound image to recognize structures using edge recognition techniques, steps 803, 804. Having recognized structures, the processor may then compare the shape and characteristics of those structures to the three-dimensional model dataset stored in memory, step 805. If a match is determined within a set margin of error, the processor may then estimate the transducer array viewing position and orientation based on the distance to the recognized structure and the angle of the recognized feature in the ultrasound image with reference to the three dimensional heart structure model, step 806. This process may also be performed iteratively wherein an initial transducer position/orientation is estimated, steps 803-806, after which the processor may scale the three dimensional structural model to reflect the expected size of structure when viewed from that perspective. Then the steps of pattern matching the structure to the modeled structure, 805, and back calculating the transducer array position/orientation, 806, may be performed using the updated match data. Such an iterative process may increase the position estimation accuracy in two, three or more iterations.

As described above, transducer array rotational angle information obtained by other mechanisms may be used in combination with image recognition techniques to more accurately determine the transducer position and orientation at the time each ultrasound image is obtained. For example, information regarding the rotational angle of the transducer array may be used by the processor to compare a particular recognized structure (e.g., the septum) to a portion of the digital three-dimensional structure model of the heart.

In addition to the above autonomous and clinician assisted methods for recognizing imaged structure, the processor may use learning system algorithms such as a neural network application to learn from clinician inputs and corrections. A neural network system may learn from determining edge locations in a series of ultrasound image frames, such as from statistical analysis edge discontinuities within frames and between frames, in order to improve the criteria used for recognizing structure. Also such a system may learn from clinician corrections to better recognize particular structures, like valves and the septum, in ultrasound images, particularly for a specific patient whose heart structures may deviate from an ideal three-dimensional model.

Figure 9:
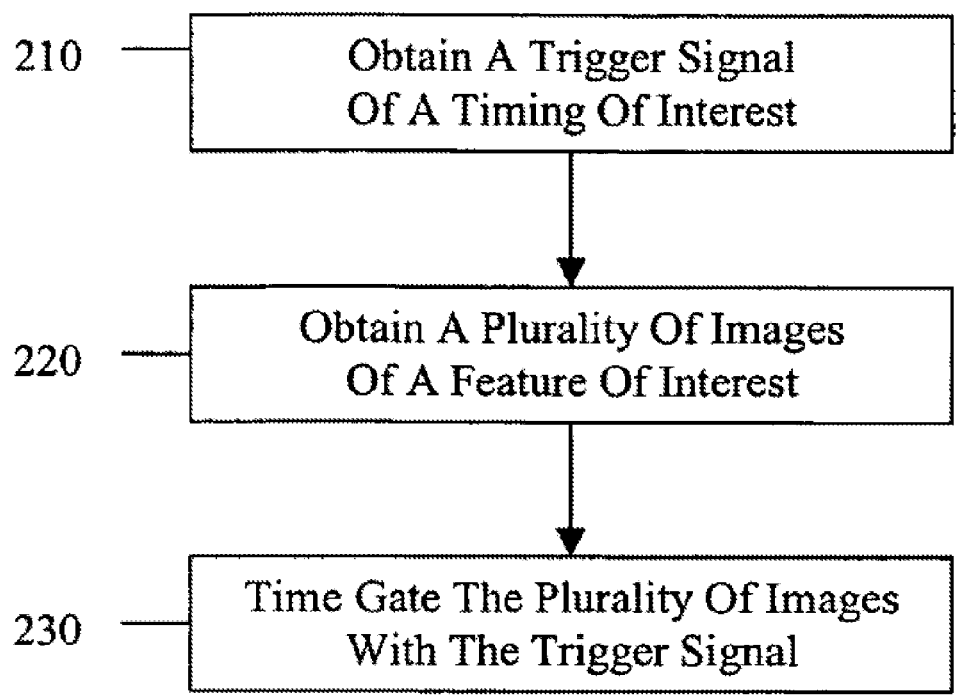
FIG. 9 is a flow diagram of an embodiment method for time-gating ultrasound images with a patient's electrocardiogram.

Solutions for imaging the moving heart: Normally, a healthy heart changes shape, contracting and expanding, in a rhythmic and repeating manner throughout the cardiac cycle. The cardiac cycle is characterized by the ECG signal which is also rhythmic and repeating. The expectation that the heart's shape changes in a rhythmically and repeating manner has been relied upon in previously disclosed methods for assembling three- and four-dimensional images of the heart from a series of ultrasound images. For example, use of the ECG signal to correlate a sequence of cardiac images is disclosed in U.S. Pat. No. 5,722,403 and U.S. Patent Publication No. 2005/0080336 which have been previously incorporated by reference. A method of time-gating a medical image to phases of the cardiac cycle according to an embodiment is shown in the flowchart of FIG. 9. This method may be performed using the medical imaging system illustrated in FIG. 1.

In an embodiment of the medical imaging system illustrated in FIG. 1, an external electrocardiogram (ECG) unit 60 may be connected to the ultrasound unit 40 through an ECG communications interface 62, with the signals sent through interface 62 used to synchronize ultrasound imaging with the heartbeat of the patient. For example, a sequence of images may be associated with a sequence of phases of a cardiac cycle, or images may be captured only at a specified phase of the cardiac cycle. The ECG signal may be monitored by the processor (e.g., microcomputer 41) to orchestrate the operation and timing of the signal generator 46 in order to image the heart at particular phases of the cardiac cycle.

Referring to FIG. 9, in step 210 a trigger signal of a timing of interest is obtained, such as from the ECG signal. In this regard, a "timing of interest" refers to any information corresponding to the display and/or analysis of images in accordance with a user's requirement based in whole or in part on a time of occurrence. By way of example, the trigger signal may comprise a periodic feature or wave within an ECG trace which may be a periodic or non-periodic signal corresponding to a physiological condition (e.g., a signal generated by an ECG probe sensing intra-cardiac electrical activity, a pacing stimulation signal, etc.), a user selection-based signal (e.g., a user selected time point in a normal or abnormal ECG trace) or other trigger signal of a timing of interest. In a normal healthy heart, the QRS complex, or more narrowly a portion of the R wave (e.g., as the transition from the Q wave to the steeply rising signal of the R wave), may serve as a reliable triggering signal that is easy for the system processor to recognize. Further, the trigger signal may be based upon a recognizable feature in the ECG trace, such as the transition to the R wave, plus a time delay. This time delay then can be increased so that a series of trigger signals spans a complete heartbeat cycle, with each time-delay trigger signal corresponding to a like portion of the ECG trace. By using such a time-delayed trigger signal, a series of ultrasound images may be obtained (or selected from memory) corresponding to like portions of the ECG trace which, presumably, will correspond to like or similar structural shapes or configurations.

As a further example, the trigger signal may be a complex and intermittently recurring ECG wave form such as may appear in a diseased heart which requires analysis of ECG signal patterns to determine the presence of the complex signal (e.g., analysis of an ECG signal to determine the presence of an irregularity to be used as the trigger signal).

In step 220, a plurality of two-dimensional ultrasound image frames of a portion of the heart are obtained and stored. This step 220 may be performed prior to, concurrent with, or after step 210.

In step 230, the ultrasound imaging system correlates or time-gates (e.g., synchronizes) the plurality of two-dimensional ultrasound image frames obtained in step 220 with the trigger signal obtained in step 210. In an embodiment, this correlating or time-gating in step 230 involves using the trigger signal obtained in step 210 to trigger generation of the plurality of two-dimensional ultrasound image frames obtained in step 220 (i.e., each image is obtained only when a particular trigger signal is sensed). By way of example, the ultrasound equipment 40 (FIG. 1) may generate ultrasound pulses correlated to the trigger signal such that an ultrasound image scan generated each time (or a set time after) a periodic trigger signal is received. In this manner, the obtained trigger signal is said to "time-gate" the plurality of images, because the plurality of images are obtained (i.e., "gated") in accordance with a timing of interest. The result will be a series of images of heart structure (e.g., heart wall, heart valve, etc.) at the same point in the cardiac cycle (within the timing errors discussed herein). If the imaged heart structure cycles through repetitive motions, the series of time-gated image frames may be combined (e.g., added or averaged) to enhance the clarity, or compared to identify irregular motions. By sequentially varying a time lag following a particular (e.g., easily recognizable) timing event (such as the Q wave), a series of time-gated image sequences may be obtained of the structure at each of a number of intervals within the heartbeat cycle. Thus, the result may be a "movie" or "motion display" of an average heart cycle.

Alternatively, the images obtained in step 220 may be stored along with or indexed by associated timing information. Such "timing information" may be any information that can be used to correlate the plurality of images with a timing of interest with respect to the dynamic condition of the heart. Such timing information may include, for example, the time that a particular ultrasound image frame is obtained, such as recording that a particular image was obtained at time "T" (plus or minus the timing errors discussed above) that also is tied to the recorded ECG data. Alternatively, the timing information may relate to a corresponding physiological condition, such as recording the ECG signal measured at the moment each ultrasound image slice is obtained. Further, the timing information may be relative to a recorded physiological condition, such as recording the offset from (time since the occurrence of) a particular wave in the ECG signal, such as time after Q wave or the rising edge or peak of the R wave in the QRS complex. In this manner, time-gating in step 230 may comprise utilizing the trigger signal obtained in step 210 to retrieve stored image frames corresponding to like portions of the ECG trace (e.g., images taken at a timing of interest) from a database of stored ultrasound image frames previously obtained in step 220 and stored by the imaging system workstation. The retrieved images may then be combined or otherwise processed as herein described.

Since time correlated or time-gated two-dimensional ultrasound image frames can be correlated to particular three-dimensional states of the heart, a series of such image frames can be used in image processing methods described herein to generate two-dimensional, three-dimensional and four-dimensional composite images. For example, several images from the same viewing perspective (transducer position and orientation) can be processed to yield composite images with improved image clarity, resolution, and/or reduce noise. As another example, several images at the same correlated time within the cardiac cycle but at different viewing orientations can be combined to generate a three-dimensional composite image.

Figure 6A:
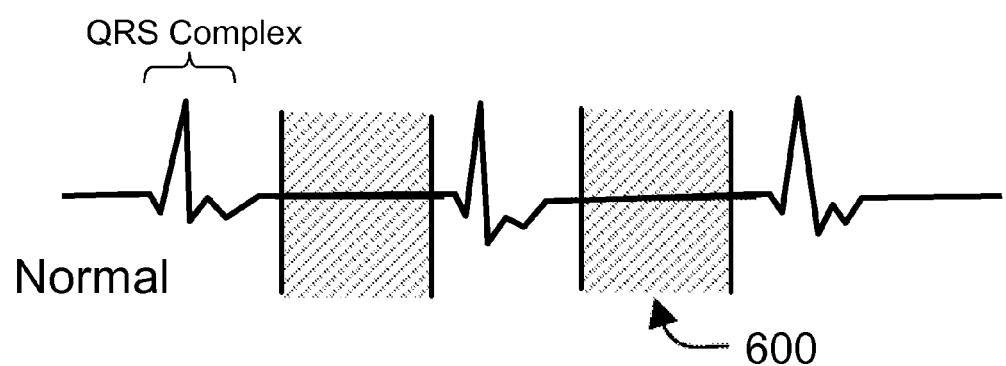
FIGS. 6A and 6B illustrate ECG signals of a normal and diseased heart.
Figure 6B:
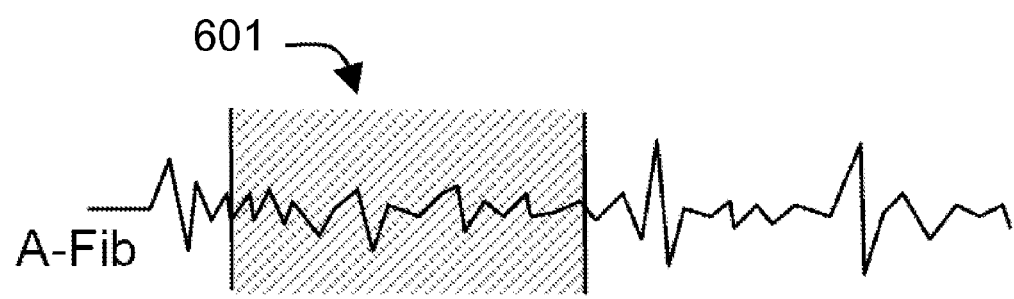

In a particular example, ultrasound image frames may be taken during the period of relative rest and relatively slow movement that a healthy heart exhibits between beats, illustrated in FIG. 6A as shaded regions 600 of the ECG. During these intra-beat periods, several ultrasound images can be obtained of the heart in the same basic shape. Since the heart is moving little during this intra-beat period 600, many of the image distortion and correlation problems caused by movement of the transducer and/or heart tissue described herein can be minimized or avoided.

While these two embodiment methods are limited to imaging the heart during diastole, the result may be an accurate three-dimensional view of the heart that can be diagnostically useful. These embodiment methods are also limited to images taken during times of normal heartbeat, when the diastole phase can be recognized from the ECG signal and the heart repeatedly returns to the same shape during moments of rest.

As another embodiment, a long series of images at various transducer orientation angles may be obtained and stored in the processor's memory along with data on the position and orientation of the transducer array at the time of each image, so that the processor can use the stored images and transducer location/orientation data to build up approximate three-dimensional images. In this example, the processor may use image processing methods that recognize similar patterns to select and stitch together images that have consistent edge shapes. This method is premised on an assumption that even in atrial fibrillation the heart returns to certain similar shapes, which can be recognized in a series of images by selecting images that can be smoothly stitched together.

The foregoing embodiment methods that enable a three-dimensional reconstruction of ultrasound images of the heart are best suited to a heart with a rhythmic cardiac cycle. However, generating a three-dimensional reconstruction of the heart may be particularly useful when the patient is in atrial fibrillation, flutter, tachycardia, or dysynchrony since causes of such conditions may be deduced from ultrasound images. In such situations, the heart is flexing in irregular and unpredictable patterns that may be disjoint from the ECG patterns. In such conditions, methods that use normal ECG signals to assist in forming a three-dimensional image may be infeasible since the position of the heart walls may be unpredictable or the ECG pattern may be erratic and random.

In cases where abnormal heart conditions exist, such as rhythm abnormalities, and where such abnormality is atrial fibrillation in particular, periods of mechanical inactivity may be brief or even absent. In such situations, multiple images may need to be acquired and processed using statistical methods to reduce the overall spatial error in the estimation of composite three-dimensional images. For example, multiple images obtained during fibrillation may be combined using a weighted averaging method wherein locations (i.e., echo locations) that appear in a majority of images within a given locale are given more weight while spots that appear in a minority of images are given less weight. Since during fibrillation the walls of the vessel (atria or ventricle) may quiver about an average shape, this averaging method may provide an image of the average shape. In this embodiment method, various averaging and estimating techniques can be used to generate a series of composite two-dimensional ultrasound images of the heart that can then be used to generate a three-dimensional image of the heart.

In another embodiment, the averaging technique uses statistical analysis of the atrial fibrillation ECG pattern in combination with edge detection analysis of ultrasound images to correlate heart wall motion or position to patterns in the ECG signal. In this analysis, the processor statistically analyzes the position of structure and associated patterns in the ECG signal. If a particular structure position occurs in conjunction with a particular ECG pattern in a statistically significant number of images (such as one or two times the standard deviation of position-to-ECG-pattern measurements), that ECG pattern may then be used to initiate ultrasound imaging or, in post-procedure processing, to select ultrasound images for processing. Once sufficient ECG and image data has been obtained so the processor can recognize correlations between ECG patterns and heart structure positions in ultrasound images, the processor can image the heart at selected times or select images in post-procedure processing that will show the heart in the same (or nearly the same) configuration based upon the ECG signal (e.g., by using statistical analysis). Then, once a series of two-dimensional ultrasound images are obtained or selected based upon analysis of the ECG signal, they can be processed and combined using the further processing embodiment methods disclosed herein.

Under such conditions of irregular heartbeat, three-dimensional reconstruction of ultrasound images may be accomplished by taking rapid ultrasound image scans over small regions by quickly imaging and rotating the transducer array between image scans. A few two-dimensional ultrasound images taken closely together in time may then be combined to render a three-dimensional image through a narrow angle of rotation. This embodiment method may be most effective when used in combination with an ultrasound imaging catheter capable of rapid rotation between image scans, such as in U.S. patent Ser. No. 11/764,194 entitled "Oscillating Phased-Array Ultrasound Imaging Catheter System" and filed Jun. 16, 2007, the contents of which are incorporated herein by reference in their entirety.

In a diseased heart, the contractions of various heart muscles may be quite rapid, out of phase, disorganized or chaotic, such that the shape of the heart does not return to the same configuration or rest on a regular or repeating basis. Such periods of fibrillation may be identified in the ECG trace as illustrated in the shaded portion 601 of FIG. 6B. Also, episodes of such erratic heartbeats may occur sporadically so it can be difficult to obtain images at a consistent point during such erratic heartbeats during the normal duration of a cardiac catheterization procedure. Under such circumstances, it may not be possible to image the heart in particular configurations, in which case the image processing methods described herein may be used to remove the blurring effect of rapid structure movement and correlate adjacent two-dimensional ultrasound image slices into a three dimensional representation of the heart.

In an alternative embodiment useful in common medical procedures involving intracardiac ultrasound imaging, the signal of interest is a pacing pulse applied to the heart such as by a pacemaker lead. When a pacemaker is implanted in the heart of a patient, the clinician may stimulate ("pace") the heart at a number of locations to identify a location which exhibits the best physiological response to the pacing pulse. Once a pacing site is located, the clinician may adjust the timing of the pacing pulses with respect to the heart cycle to determine the phase lag or lead which results in the best physiological response to the pacing pulse. This procedure may be conducted under the observation of intracardiac ultrasound imaging to assist the clinician in locating the electrode as well as observing the physiological response of the heart. In this embodiment, the pacing stimulation is used as the timing signal, which will be detected in the ECG signal, to time-gate ultrasound image frames as described above. Using this embodiment in combination with the image processing methods described herein, the clinician can obtain image frames which characterize the heart during pacing stimulation, both at the point of stimulation and at selected time intervals following stimulation.

In an alternative of this embodiment, the stimulation pulse may be applied by the clinician in order to initiate or terminate fibrillation. In such a procedure, the stimulation is used to induce the heart to enter into a condition that is being diagnosed, such as episodic fibrillation, or to terminate an irregular heart beat. In such cases the stimulation pulse can be used as a triggering signal to obtain (or recall from memory) ultrasound image frames to image the heart as it undergoes a transition into or out of a fibrillation or other irregular heart beat condition.

Methods for processing images of the moving heart: Ultrasound image frames taken of the heart, particularly during periods of rapid movement, can be processed according to the following embodiment methods in order to overcome the challenges described above.

Figure 10:
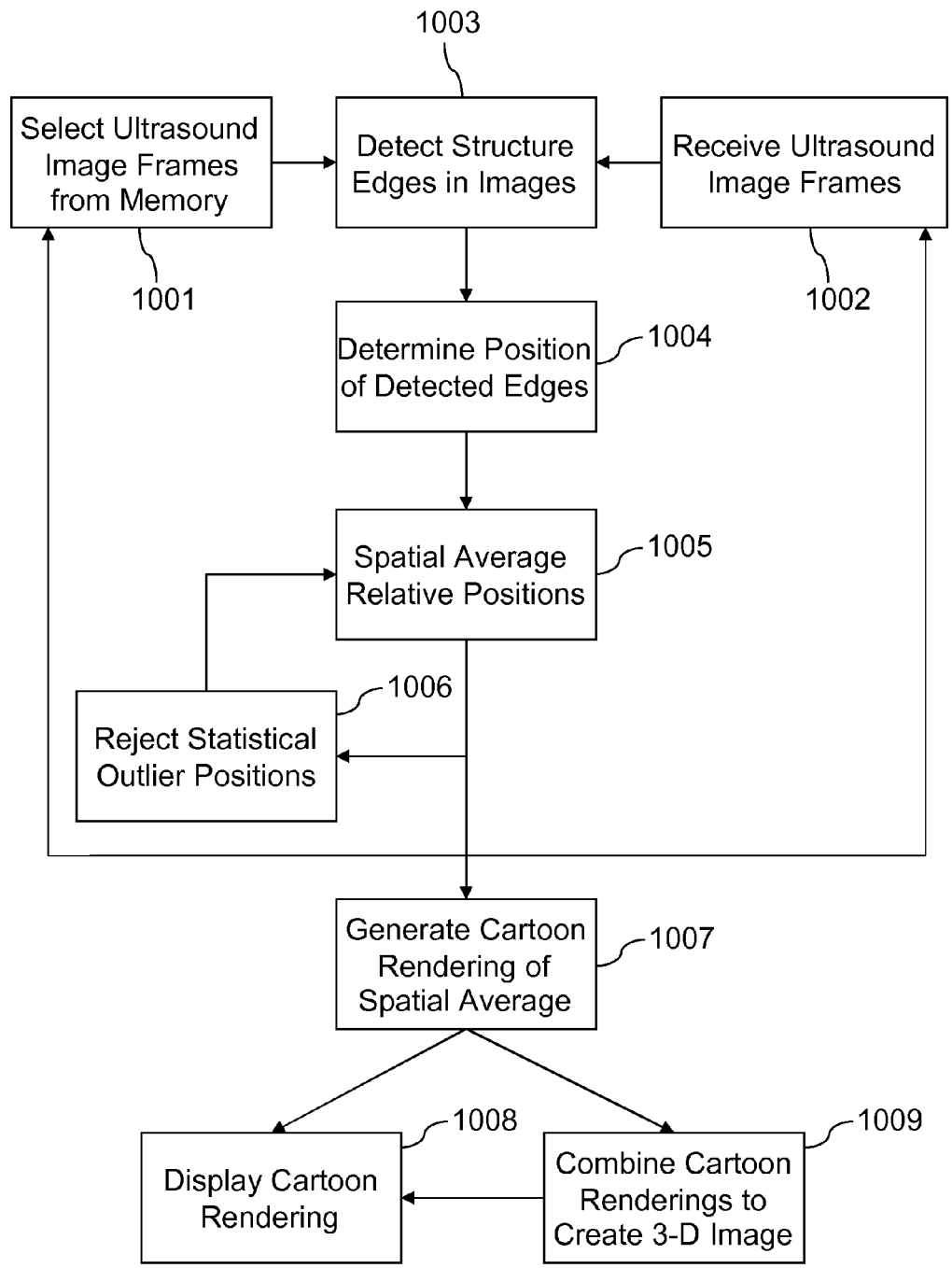
FIG. 10 is a flow diagram of an embodiment method for processing ultrasound images to enable construction of a three-dimensional image.

In an embodiment method illustrated in FIG. 10, many of the challenges of processing and combining ultrasound images of the moving heart are managed by using statistical processing of spatial data derived from images instead of statistical analysis of image data itself. If image data from several ultrasound images of a moving organ are statistically analyzed, the result can be a blurring of the image. While statistical analysis of individual pixels as described above can remove random noise features, such as speckle and electronic noise, the same analysis can result in composite images with blurred edges as movement of tissue from frame to frame will be statistically combined with image location errors and other ultrasound image uncertainties. To avoid this effect, the embodiment method first recognizes the location of structure and determines its spatial coordinates, and then statistically analyses the spatial coordinate data to of recognized structure in multiple image frames determine the most likely location of the structure in a composite image.

Referring to FIG. 10, in this embodiment method, ultrasound image frame data may be retrieved from memory (e.g., from image frames stored in the memory of the ultrasound imaging system or in a database), step 1001, or received directly (i.e., in real time) from the ultrasound imaging system, step 1002. Individual ultrasound image frames are processed by a programmable processor, such as the workstation of the ultrasound imaging system or an image analysis workstation, to detect structures using edge-detecting image processing algorithms, step 1003.

As discussed above with reference to FIG. 8, edge-detecting image processing algorithms determine the edges of structures by noting a sudden change in pixel brightness along image radians. For example, for some structures, the processor may compare the brightness (i.e., amount of reflected ultrasound) versus distance along each ultrasound beam to detect a sudden rise over a short distance (e.g., large Δbrightness/Δdistance) and determine that an edge exists at a pixel where this rate of change exceeds a threshold. As another example, which may be used alternatively or in addition to the first example, the processor may first determine that a structure exists in a portion of an image frame and then determine the edge of that structure. In this second example method, the processor may first recognize that a structure exists along a portion of a radian by noting that the portion has a higher average brightness than other darker portions where there is no structure (i.e., the darker portions contain blood which reflects less ultrasound). Once a structure has been recognized, the processor can compare brightness values of pixels along a line segment spanning the determined structure and a portion of the darker region to determine where the edge of the structure exists. This determination may be based upon a number of criteria, such as for example: (a) a point of inflexion of the brightness versus distance along this line segment, (b) a pixel with an intermediate brightness value (such as the pixel closest to the median brightness value, or the pixel having a brightness value that is some fraction of the difference between the average bright and average dark region pixels) between the darker region and the brighter region, (c) the first pixel in the segment with an increased brightness over the darker region, or (d) the first pixel in the segment that has brightness value approximately equal to or greater than the average brightness in the bright region.

When the processor recognizes that a structure edge exists at a particular location, the coordinates of the recognized structure are stored as the positional measurements (e.g., X, Y, Z coordinates) of the edge locations or as vector or tensor coordinates (e.g., as a three-dimensional vector), step 1004. The positional measurements are first obtained with respect to the transducer array at the apex of the image, such as radial angle transducer orientation angle, and distance values along each radian in the image frame. Optionally, the radial coordinate values may be converted to rectilinear X-Y-Z coordinates using well known transformation algorithms. This process generates a three-dimensional spatial dataset defining the locations of structure surfaces. If the back edge of a structure is imaged, the dataset will include the spatial coordinates of both the front and back edges of a structure, and a further processing algorithm can recognize that the two edges define the same structure. This algorithm may be as simple as a rule that closely spaced edges are associated with the same structure. The processor may thus define and store a volumetric structure dataset which spatially locates the structures recognized in the ultrasound image.

The process of recognizing structures, step 1003, and recording the spatial coordinates of recognized structures, step 1004, extracts structure location data from ultrasound image data, thereby generating an image dataset that can be statistically processed without compounding the errors and data uncertainties inherent in ultrasound images.

The processor can then statistically process structure spatial (i.e., location) data across some or all of the image frames to determine an average, most likely or best fit location for the structure, step 1005. Statistically processing the spatial location of edges allows the processor to select for display a single representative location for each structure edge from a multitude of images, with that single representative location being a close approximation to the nominal position of the structure.

This process step is based upon the observation that heart structure is constrained and thus moves (in and out, back and forth) about a central location. For example, the ventricles pump blood by first expanding to increase their volume and then contracting to decrease their volume, and as a result the ventricle walls first move outward and then inward in approximately equal distances with respect to their nominal position. As a first approximation, the central location of a constrained structure is the average of the spatial locations of the maximum and minimum volume locations. As another example, heart tissue in fibrillation may move rapidly but it does so about a nominal position. Thus, the nominal position of a constrained structure that is moving can be estimated by averaging (or other statistical calculation) the spatial coordinates of the structure across a number of image frames. The more images that are spatially averaged in this manner, the closer the average position will be to the nominal position of the constrained structure. The estimated nominal position can then be used as the representative position for generating an image of the heart structure (referred to herein as a representative image).

Statistically processing the spatial location data for structures to determine a representative location can provide better results than other methods when the heart is moving rapidly and/or irregularly, as may happen in a diseased heart undergoing fibrillation. In such cases, it may not be possible to "time-gate" ultrasound images or otherwise select images that correspond to the same shape or configuration. In many diagnostic situations, the shape of the heart during fibrillation is of greater importance than during normal heart beats. Also, during fibrillation the heart structure may move too far between image frames or between transducer rotational orientations to permit the transducer to obtain ultrasound images of the structure in the same shape or configuration. This analysis method compensates for the effects of rapid movement by calculating a single spatial representative location for each image point on a structure that lies close to the center of motion. While the selected representative spatial locations do not reflect the location of structure at any particular point in time, the resulting image of the structure is representative of the nominal structure of the heart and therefore useful for diagnostic purposes.

The processor may use a number of statistical analysis methods to determine a single representative location for the structure from a series of image frames. These methods include, for example, computing a simple average of the spatial location in all images, determining the mean or median spatial location in all images, and computing a weighted average location which may incorporate statistical information or knowledge about the nature of the structure being imaged in the form of weighting factors. For example, a weighted average analysis method that can be used to determine a single representative position may first determining the average of all the spatial locations, and then compute a weighted average where each spatial location value is weighted based upon its distance away from the average location.

In an optional step 1006 the processor may analyze the spatial location data among a number of images to determine statistical values of average locations and standard deviations about those locations, and then identify image frames in which the location values appear to be outliers. Outlier locations may be identified as locations that are more than one or two standard deviations from the average location, or other criteria that may be set. The processor may then ignore the outlier image location data in determining the average (or median) location of each structure. Thus, in this optional combination of steps 1005 and 1006, the processor may determine the representative location of a structure as the average of locations excluding the outlier locations (e.g., locations exceeding 2 standard deviations from the average), the median of locations excluding outlier locations, or some other location determined statistically from the location data excluding outlier locations.

The steps of selecting or obtaining an image frame, steps 1001, 1002, detecting edges in the images, step 1003, determining the spatial locations of edges, step 1004, and determining the average (or other statistical measure) spatial location of the edges, step 1005 and optional step 1006, are performed for all or a subset of the image frames. In an embodiment, these process steps are performed for a subset of image frames obtained from a particular transducer rotational orientation. These steps are repeated for subsets of image frames corresponding to different transducer rotational orientation until a cartoon rendered image frame has been generated for all transducer orientations spanning the range of transducer rotational orientations in order to generate a spatial location dataset spanning the entire imaged volume of the transducer array.

Working with a single image frame or the spatial location dataset corresponding to a particular transducer rotational orientation, the processor can then generate a "cartoon" rendering of the structure detected in a single two-dimensional image frame by linking together all of the average edge locations that form a line in the image, step 1007. In this step, the processor compares adjacent locations in the image frame to determine if they are part of the same structure. This determination may be a simple comparison to evaluation criteria such as closeness in space or relationship to a line of locations. If a series of spatial locations are determined to be the same structure, the locations are linked by a line, or replaced by a line whose spatial dimensions (locations, vector coordinates, etc.) are stored in memory instead of individual location coordinates. Isolated point locations are left as is since such edge detections could be a structure viewed edge on such that it will appear as a line in a three-dimensional image but only as a point in a two-dimensional slice image. Since the lines and surfaces reflect average spatial locations rather than images themselves, these generated features are referred to herein as a "cartoon rendering" of structure rather than a two- or three-dimensional "image." This process step can be repeated for all image frames.

By cartoon rendering the average location of detected structure in image frames corresponding to a particular transducer rotational orientation, a clean two-dimensional image of heart structure in its nominal position (as viewed in the particular transducer orientation) can be displayed for the clinician, step 1008. This cartoon rendering display may have diagnostic benefits since it will cleanly reveal the nominal (e.g., average) shapes of structures without interference of noise or speckle and without the blurring caused by rapid movement of heart tissue. Thus, this process provides an image of the nominal shape of the heart even when it is in fibrillation.

The processor can also generate a three-dimensional cartoon rendering of the entire imaged volume by combining the cartoon rendered image frames for all transducer rotational orientations or generating a three-dimensional cartoon rendering from the entire three-dimensional spatial location dataset, step 1009. In this step, the processor compares adjacent average image frames to determine which edge locations are associated with the same structure and connect such edge locations with a line or surface spanning the adjacent average image frames. Information regarding the transducer rotational orientation, which may be stored or correlated with the image frames, is used by the processor to determine the spatial separation between adjacent image frames. Since the transducer is rotated about its long axis between adjacent image frames, the spatial separation between points and lines in the two images depends upon their distance from the transducer and the angle between the adjacent image frames, a factor that the processor easily calculates using simple trigonometric formulas. The processor then generates a line between isolated edge points in adjacent image frames, which may appear when a structure (e.g., a valve surface) is imaged edge on in the two-dimensional image frames. The processor generates a surface between lines in adjacent image frames, which will occur when a structure is imaged face on (e.g., the septum 16 imaged from the right ventricle as illustrated in FIG. 2). This process can be repeated for all adjacent image frames until a full three-dimensional set of lines and surfaces have been defined that link together all of the average spatial locations of detected edges in the dataset. The result is a line and surface rendition of the tissue structures imaged in all of the ultrasound images.

The processor may use a variety of algorithms to connect adjacent cartoon rendered image frames. The processor can recognize that points or lines in one image frame are part of the same structure imaged in an adjacent frame by comparing their separation distance to threshold values. Then, the processor can determine a line or surface which connects related points and lines together to span the volume contained within and between the adjacent image frames. The connecting line or surface can be stored as a vector or tensor value in order to reduce the amount of data required to describe the structure in three-dimensional space.

Instead of working from two-dimensional cartoon renderings, the processor in step 1009 can work directly from the three-dimensional spatial location dataset to generate a three-dimensional cartoon rendering of the imaged volume. Information regarding the transducer rotational orientation stored or correlated with the image frames is used to determine the spatial separation between adjacent image frames. A variety of algorithms may be used to connect average edge locations in adjacent image frames to generate the cartoon lines and surfaces in step 1009. In a first example algorithm, the processor first determines the correspondence of the points and lines in adjacent image frames, such as by comparing the spatial coordinates of the points/lines to determine whether two points/lines are positioned closely together (i.e., within a tolerance limit) in the two frames, and then calculating a vector or surface which links together the corresponding points and lines through the space between adjacent image frames. Algorithms for comparing spatial locations within a tolerance and interpolating between two special coordinates are well known in the computer programming arts or within the ordinary skill of a computer programmer. A second example algorithm compares the spatial location information in two or more, or even all image frames and determines best-fit lines and surfaces that connect the spatial locations together. Algorithms for generating best-fit lines and surfaces for connecting spatial location data are well known in the computer programming arts. This process may be iterative by which the processor makes a first estimate of the best-fit from frame to frame, and then repeats the process across all frames to smooth out discontinuities and inconsistent interpolations. A third example algorithm assembles all image frames into a three-dimensional rendition and then generates intra-frame connecting lines and surfaces by geometric interpolation.

As part of generating a three-dimensional cartoon rendering, step 1009, the processor may smooth out the connecting lines and surfaces among the image frames. For example, the processor may test the rendered lines and surfaces for sudden changes in direction. If a line or surface makes a deviation that exceeds a threshold (e.g., exhibiting an angle greater than a threshold), the processor may adjust the shape of the line or surface to provide a smooth transition, such as by implementing a quadratic or cubic best-fit curve between or among points in three or four adjacent image frames. Alternatively, the processor may use a spatial location value that is slightly removed from the average spatial location in a particular frame in order to enable a smooth connection across three or four adjacent image frames. In determining whether lines and surfaces should be smoothed, the processor may employ evaluation criteria that take into account knowledge of the properties and nominal shapes of heart tissues and structures.

The result of the three-dimensional cartoon rendering step 1009 may be a new three-dimensional spatial dataset of lines and surfaces. This dataset may be much smaller in terms of stored information as lines and surfaces may be represented as vector and tensor values, thereby eliminating the need to store individual spatial location data from all of the image frames.

With a three-dimensional cartoon rendering dataset in memory, the processor can then generate a three-dimensional display of the structures, step 1008. Any of a number of well known methods for displaying three-dimensional image data may be employed, including perspective projections, rotating displays, and adjacent rotated perspective views. Also, well known display methods and algorithms may be used to allow the clinician to manipulate the display, such as rotating the image, zooming in or away from the image, and moving into or out of the image.

To use this embodiment method, a clinician may obtain several ultrasound images of the heart over a few cardiac cycles and then rotate the ultrasound transducer (e.g., by rotating the handle of the catheter slightly) to change the imaging perspective, particularly the rotational orientation. The ultrasound images are stored in a dataset that includes or is correlated to data indicating the rotational orientation of the transducer. By imaging over a few cardiac cycles, rotating the catheter, and then repeating the process, the clinician can obtain a large dataset of two-dimensional ultrasound slice images spanning a partial or complete rotation of the transducer array that can be processed using this embodiment method. Optionally, ECG data may also be recorded in the dataset for selecting image frames which correspond to like portions of the ECG trace for further processing together.

Figure 11:
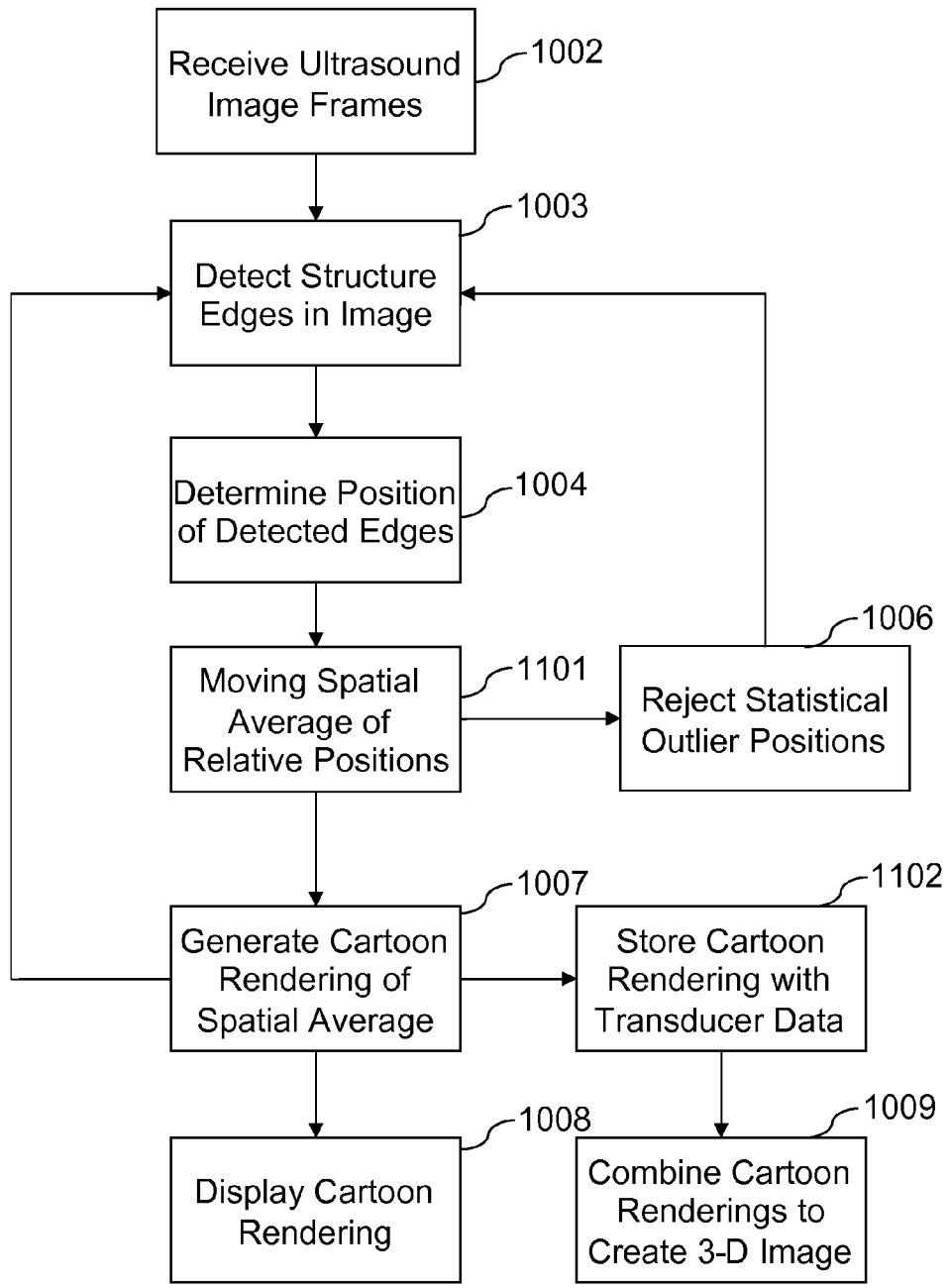
FIG. 11 is a flow diagram of an alternative embodiment method for processing ultrasound images to enable construction of three-dimensional images.

While the foregoing method assumes that the processing is accomplished after the ultrasound images have been obtained, i.e., in post-procedure processing, the method can also be used to obtain and generate live cartoon rendered images, as illustrated in FIG. 11. In this alternative embodiment, the steps of receiving ultrasound images from the ultrasound imaging system 1002, detecting structure edges 1003, and determining the spatial location of detected edges 1004, are performed as described above with reference to FIG. 10. Instead of averaging the spatial locations of detect edges in all images, a moving average of the spatial positions of detected edges is obtained from a subset of the stream of images, step 1101. In this step, the spatial location data from a selected number (greater than two) of ultrasound image frames in a series of image frames are used to determine nominal special location data using statistical methods (e.g., average, mean or other statistical measure as described above) in a manner that updates as more images are obtained. For example, the nominal position data may be obtained by taking the average of the spatial position data in five consecutive image frames, with the average being updated with each subsequent frame by including its spatial data in the average and disregarding data from frames older than five frames back in time. The result is a moving average of spatial location data that is used as the nominal position of the detected edge. The number of image frames used in calculating the moving average may be anything more than two frames, although it is believed that averaging more than five to seven frames worth of spatial data is unlikely to result in a significantly more representative or accurate representation of the heart.

Using the moving spatial average positional data derived in step 1101, the processor can identify and reject outlier images or spatial position data, step 1006. The processor can also generate a cartoon rendering of the spatial average edge position data, step 1007, that is provided as a display for the clinician, step 1008, using methods similar to those described above with reference to FIG. 10.

This alternative embodiment is well suited for generating a real-time nominal image of a rapidly moving heart, such as a diseased heart in fibrillation. In this embodiment, the cartoon rendering of image frames is accomplished at the same time as images are obtain. Consequently, there will not be a three-dimensional spatial dataset available for simultaneously generating a three-dimensional composite image. Accordingly, the processor may store the cartoon rendered spatial information (e.g., vector and tensor data) in a dataset as such data is generated, step 1102. The stored cartoon rendered spatial information may include or be correlated with data describing the rotational orientation and position of the transducer array. With such a dataset, the processor can then combine the cartoon renderings to create a three-dimensional image or dataset, step 1009, according to the various methods described above with reference to FIG. 10.

Methods for processing images to remove noise and distortions: Ultrasound image frames processed using the foregoing embodiment methods will remove much of the noise and image distortions inherent in ultrasound images. By recognizing structure and representing the best structure location with a cartoon image, random pixels from noise, speckle, and multipath interference, as well as volumetric and timing distortions can be significantly reduced or completely eliminated. Additionally, ultrasound images may be processed according to the following embodiment methods in order to further overcome the noise and distortion challenges inherent in ultrasound images.

As explained in U.S. Patent Publication No. 2005/0080336 A1 which was previously incorporated by reference, a number of images of the same structure of the heart in the same shape (e.g., at rest or during the same point within the cardiac cycle) can be used in a processing method to average out, subtract out, or identify and ignore noise. These multiple images can be averaged or combined by the imaging system workstation to provide a composite image having a greater signal to noise ratio than present in any single image.

By way of example, each pixel in a plurality of images may be tracked and compared to a threshold occurrence level (e.g., number of images in which the pixel exceeds some threshold value) to eliminate spots (i.e., bright pixels) that do not appear in at least a specified number of images. Each point or pixel in the various images can be inspected to determine if an image value, or narrow range of values, is present in the pixel in more than one image. If a particular pixel value (e.g., "0" indicating no echo) is present in a majority of images, a corresponding value can be assigned to the pixel in the compound image. In this manner, a composite image can be assembled reflecting the most common pixel values present in the various images. The threshold percentage of images containing a value required to set a corresponding pixel in the composite image may be adjusted from, for example, a significant minority, to a simple majority to a supermajority as desired to reduce noise or increase sensitivity. Alternatively, the value assigned to a pixel may be based upon an average of the values for the pixel in the various images, with average values below an adjustable threshold set to zero to eliminate random speckle.

Noise pixels, such as speckle, will tend to be eliminated from a composite image generated using this method because they occur randomly in ultrasound images and therefore will not appear at a given pixel in a majority of images. Conversely, structure will tend to be enhanced in such a composite image because echoes from structure will be received in a majority of images.

In an embodiment of the present invention, pixel values in a composite image may be established based upon pixel weighting factors applied to the pixels in the processed images to obtain a weighted average processed or composite image. Such weighting factors may be determined statistically based upon analysis of some or all of the ultrasound image, such as in an iterative or moving average analysis manner. For example, pixel values indicating the strength of the received echo (i.e., amplitude) may be used to generate a weighting factor for averaging, such as large (i.e., bright) pixel values may be given a higher weighting than pixels with low or dim pixel values. This approach recognizes that structure is more likely to return a bright echo than a random noise event. As another example, the weighting factor applied to pixel averaging may vary as a function of distance from the transducer to compensate for the decline in signal-to-noise ratio with imaging distance.

Figure 12:
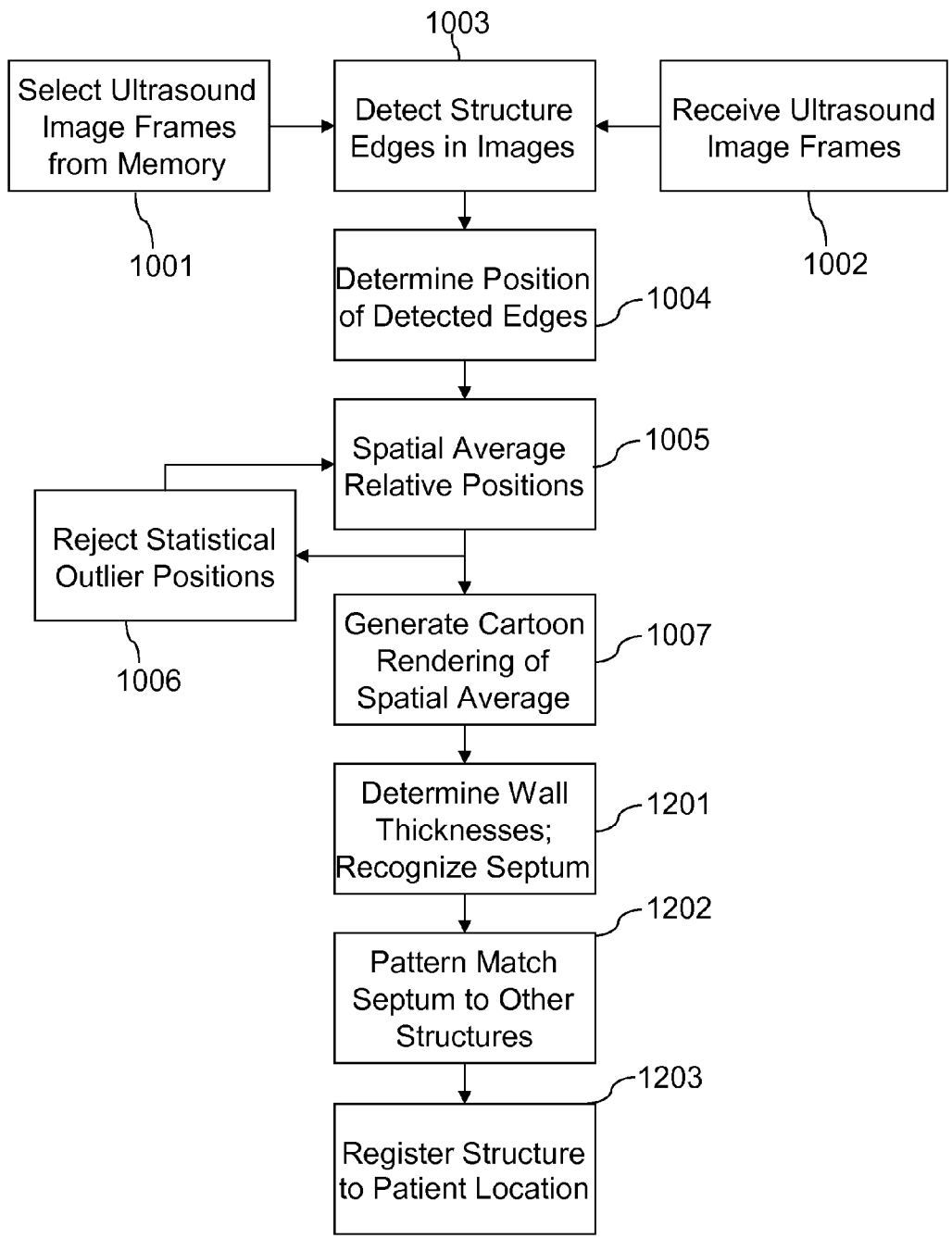
FIG. 12 is a flow diagram of an embodiment method for processing ultrasound images to register imaged structure within an external coordinate reference frame.

Methods for processing images to register to an external reference frame: Ultrasound image information can be processed to locate or register the image data within an external frame of reference according to the following method embodiment. An example of this embodiment is illustrated in FIG. 12. In this embodiment, the steps of receiving ultrasound images from memory 1001 or the ultrasound imaging system 1002, detecting structure edges 1003, determining the spatial location of detected edges 1004, and generating a cartoon rendering of the spatial averaged structure are performed as described above with reference to FIG. 10. Using the cartoon rendered spatial structure data, the processor analyzes the structure to recognize particular features, step 1201. Be measuring the thickness and relative locations of structure, the processor can match the cartoon rendering to expected structure shapes and sizes as stored in a table of values or a three-dimensional digital model of the heart. In particular, the septum has a thickness and is positioned prominently between the ventricles in many imaging perspectives, so the septum can be easily identified by the processor based upon its wall thickness and/or position within the image frame. For example, when imaging the left ventricle from within the right ventricle, the structure closest to the transducer will normally be the septum. In other viewing perspectives, such as when viewing across the atrial portion of the heart, other structures may be recognizable, such mitral valve or bicuspid valve. The processor notes the spatial coordinates and orientation of the recognized structure (e.g., the septum).

Recognizing the septum or other structure in step 1201 provides information on the location of the ultrasound image within the heart, but not enough to accurately locate the image within the heart of the patient. For example, if the processor determines that the septum is located 2 cm from the transducer array, this does not locate the transducer with respect to the long axis of the septum. To accurately locate the image, further structure must be recognize in step 1202. In this step, the processor evaluates the shape, position and orientation of other structure in the image with respect to the recognized structure (e.g., the septum) by comparing it to a three-dimensional digital model of the heart. For example, in FIG. 2, the span of the ultrasound image 26 encompasses a portion of the left ventricle wall 15 and a portion of the left atrium as well as the septum. Using the position and orientation of the septum with respect to other structure, the processor compares their sizes and relative positions and orientations to a three-dimensional digital model of the heart to determine a most likely location of the image. This pattern matching may be accomplished by geometric transformation algorithms which manipulate the digital model of the heart until a close match with the cartoon rendered structure is determined. Based upon this match, the processor can locate the ultrasound image frame within the heart.

The processor can then align, locate or otherwise register the ultrasound image within the patient, step 1203. This may be accomplished by recognizing structures, such as a ventricle wall, that has a known location within the patient. Alternatively, a recognized structure, such as the septum, may also be located using fluoroscopy, so the position of the cartoon rendering can be correlated to the external frame of reference of the fluoroscopy system. In yet another alternative, the transducer itself may be imaged by fluoroscopy, allowing its position to be determined within the external frame of reference of the fluoroscopy system. Also, other devices located in, on or near the heart, such as electrophysiology catheters or pacemaker leads may appear in both the ultrasound image and a fluoroscope image, allowing the cartoon rendering to be registered directly with the fluoroscopy system. Additionally, two or more of these methods may be employed simultaneously to more accurately align the ultrasound image within the external reference frame.

Figure 13:
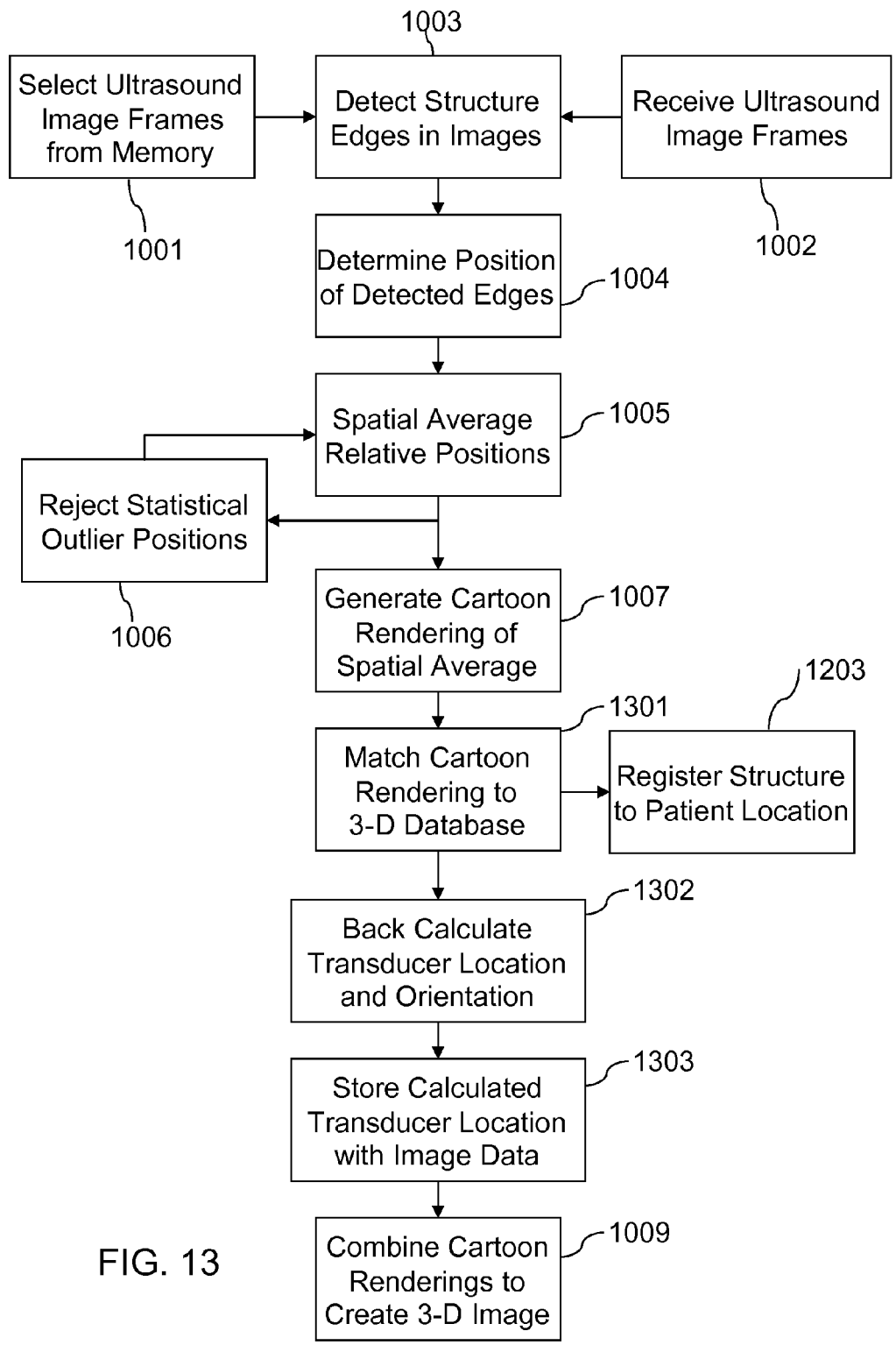
FIG. 13 is a flow diagram of an alternative embodiment method for processing ultrasound images to enable construction of three-dimensional images.

In an alternative embodiment illustrated in FIG. 13, the process of recognizing structures and correlating them to a three-dimensional model of the heart can be used to also determine the imaging perspective of the transducer. In this embodiment, the steps of receiving ultrasound images from memory 1001 or the ultrasound imaging system 1002, detecting structure edges 1003, determining the spatial location of detected edges 1004, and generating a cartoon rendering of the spatial averaged structure are performed as described above with reference to FIG. 10. Using the cartoon rendered spatial structure data, the processor then matches the cartoon rendering to a three-dimensional digital model of the heart, step 1301. This matching of the cartoon rendering to the model heart may be accomplished using the methods described above with reference to FIG. 12. Alternatively, all of the structure lines in the cartoon rendering may be compared to the three-dimensional digital heart model, such as by rotating and slicing the model using a variety of geometric transformations, until a best fit position and orientation is identified.

Once a best fit of the cartoon rendering within the three-dimensional digital heart model is obtained, the processor can register the cartoon rendering within the patient or within an external frame of reference, step 1203, using some or all of the methods described above with reference to FIG. 12.

Using the position of the cartoon rendering within the three-dimensional heart model, the processor can determine the transducer location and orientation by back-calculating, step 1302. In this step, the distance to and orientation of recognized structure, along with the actual position of this structure in the heart model, are used to estimate the point of origin of the image. Any of a number of image processing algorithms may be used for this process, including ray tracing and triangulation techniques.

The processor can then store the calculated imaging perspective (i.e., transducer position in space and orientation with respect to its three axes of rotation) along with the cartoon rendered image in an image dataset, step 1303. This information may be stored within the dataset, such as the position and orientation of the point of origin of the cartoon image, or stored as a correlated dataset linked to the image dataset by a shared key, pointer or other reference.

Finally, after all of the ultrasound images have been received and processed, the processor can use the information in the resulting dataset to generate a three-dimensional cartoon rendering of the heart, step 1009, using any of the methods described above with reference to FIGS. 10 and 11.

In a variation to this embodiment, the precise transducer array position and orientation information obtained by various embodiments may be combined with the structure registration information obtained by image processing in order to more accurately align or register the two-dimensional, three-dimensional or four-dimensional ultrasound images within the patient or with respect to an external frame of reference. In this embodiment, the estimated transducer array position and orientation information provided by sensors built into the catheter may be combined with X-ray or computer tomography (CT) scan data to more accurately register the ultrasound image data within the X, Y, Z coordinates of a patient-centered or external centered frame of reference. In this manner, structures detected in the ultrasound images (i.e., sources of ultrasound echoes) can be located at relatively precise points (e.g., at specific X, Y, Z coordinates) within the external frame of reference. In this manner, registration errors can be reduced by essentially combining two or more independent methods for correlating or registering the ultrasound images with respect to an external coordinate frame of reference. By correlating or registering the two-dimensional, three-dimensional or four-dimensional ultrasound image sets within a patient or external frame of reference, the ultrasound image data may then be fused with other image data (such as X-ray or CT scan data) to produce high quality, multi-sensor images of the patient.

One method for locating ultrasound transducers within an external frame of reference employs fluoroscopy to image the catheter while ultrasound images are obtained. Methods for locating the position and orientation of ultrasound transducer arrays within a patient using fluoroscopy are disclosed in U.S. patent application Ser. No. 11/610,386 previously incorporated by reference. In such methods, the X-ray source and imaging plane are at known coordinates within an external frame of reference, so the transducer array position and orientation can be determined with respect to that frame of reference. Using this information, the processor can correlate the ultrasound images taken at the same time the transducer array is localized using fluoroscopy to the external frame of reference by coordinate transformations using well known algorithms.

Figure 14:
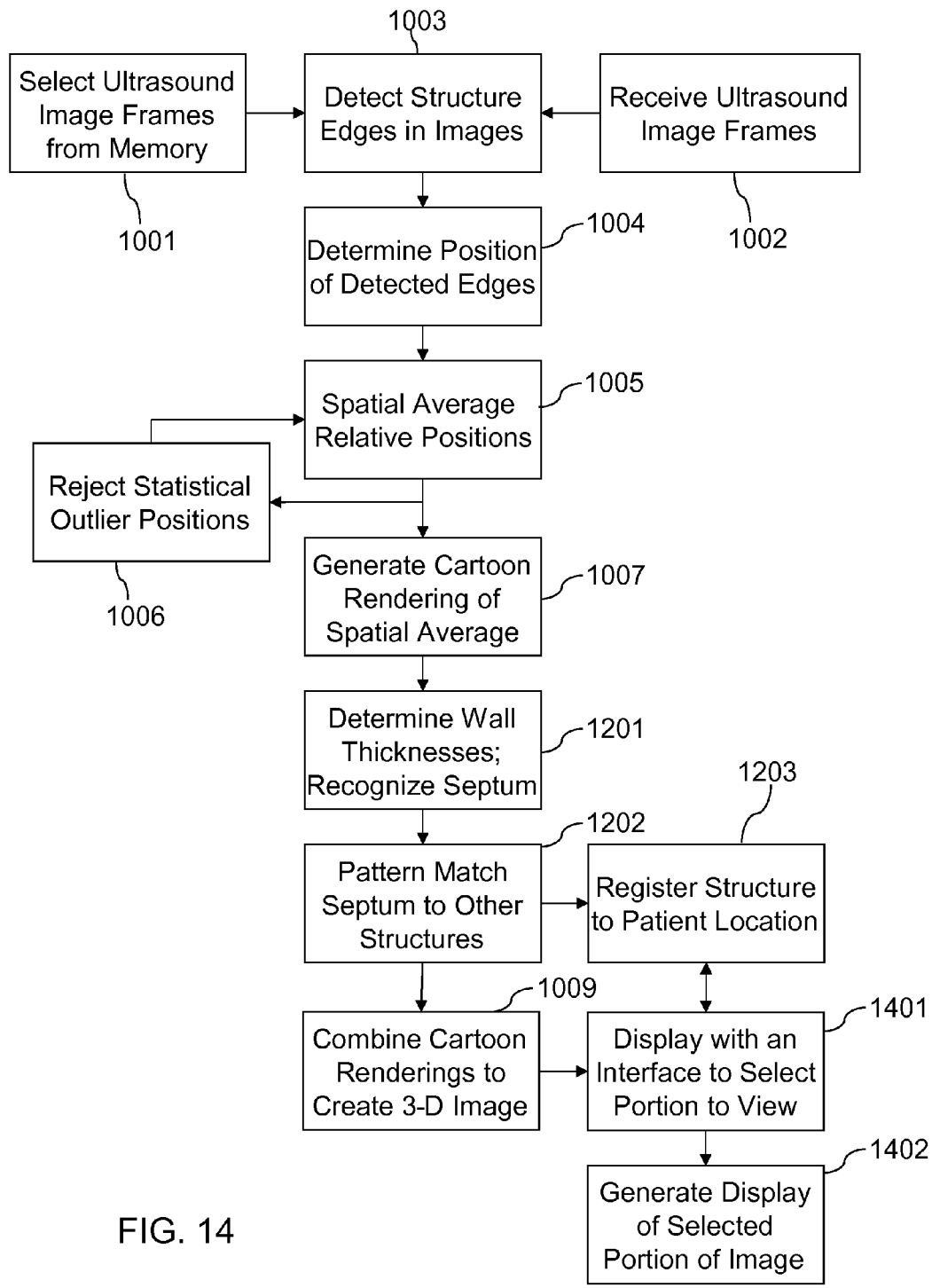
FIG. 14 is a flow diagram of an embodiment method for processing ultrasound images to enable a user to obtain detailed image data of a selected portion of an imaged organ.

Solutions for processing images to provide an improved display interface: Using image data obtained according to the various aforementioned embodiments an improved display of ultrasound images can be provided to enable clinicians to study details of the display from different perspectives. An example of this embodiment is illustrated in FIG. 14. Having generated a three-dimensional dataset of heart structures within the imaged volume, a processor can manipulate this data to generate displays of the heart according to a clinician's specifications.

Referring to FIG. 14, the process steps of receiving ultrasound images from memory 1001 or the ultrasound imaging system 1002, detecting structure edges 1003, determining the spatial location of detected edges 1004, and generating a cartoon rendering of the spatial averaged structure are performed as described above with reference to FIG. 10. Similarly, the process steps of recognizing a reference structure like the septum 1201, pattern matching the recognized structure to other structures and to a three-dimensional digital model of the heart, step 1202, and registering the cartoon rendered image to the patient or an external frame of reference, step 1203, are performed as described above with reference to FIG. 12. The cartoon rendered images can then be assembled into a three-dimensional dataset, step 1009, using the methods described above with reference to FIG. 10. As noted above, the result of these image processing steps will be a three-dimensional dataset that summarizes the structural information that could be derived from a large number of ultrasound image frames. To provide greater utility to the clinician, the processor can be configured by software programming to provide an interactive display.

Providing the interactive display includes providing a display of the three-dimensional cartoon rendered image while providing the user with an interface for designating, zooming or selecting a portion of the three-dimensional image for viewing, step 1401, and then generating a display showing the selected portion of the three-dimensional image, 1402. The user interface may be any sort of user interface well known in the computer science arts, including a touch screen, graphical user interface (GUI) with pointer (e.g., a mouse or light pen), and/or a set of user commands enterable via a keyboard input device. The user interface may include menus on the display for indicating the options the clinician has for investigating the three-dimensional image dataset. The display included with the user interface may be a view of the cartoon rendered three-dimensional image, which may be rotated, zoomed in or out, or cut into cross sections in response to user inputs, such as by a pointer or keyboard input device.

In providing the display interface, the processor may also show information relating the displayed image to an external reference frame, such as with respect to the patient's body. In doing so, the processor may provide the clinician with options for viewing portions of the cartoon rendering from perspectives related to the patient's body or external equipment. For example, the clinician may use the information in the display interface to view a portion of the heart as it would be seen during open heart surgery (i.e., from the chest) or the perspective imaged by a fluoroscopy system.

In response to inputs from the clinician, the processor accesses the cartoon rendered three-dimensional image dataset and calculates a perspective that corresponds to the requested view. Using the calculated perspective, the processor then generates a view of the cartoon rendering as would be viewed from that perspective sized to fill the area of the display. Since the cartoon rendering is stored as a vector or tensor dataset, the generation of the perspective view can be accomplished using geometric transformation algorithms well know in the computer science arts.

This embodiment allows the clinician to fully interrogate the information contained within the ultrasound image data including the ability to view structure from perspectives not directly viewed in ultrasound images and with zoom capability without the distraction of ultrasound noise and speckle.

Overall Image Processing Procedures. The foregoing imaging and image processing embodiments may be used together or in sequence to provide diagnostically useful information. In a typical ultrasound imaging procedure, the clinician will position the ultrasound imaging catheter within the heart of the patient using fluoroscopy (or other means) to guide the transducer to the desired location. The transducer location and orientation may be confirmed by the clinician viewing some preliminary ultrasound images on the system display. When the clinician is satisfied with the ultrasound transducer's viewing perspective, the clinician may initiate the capture of ultrasound images, recording of the transducer location and rotational orientation data, and (optionally) recording ECG data (e.g., using electrophysiology equipment). The ultrasound image, transducer location/orientation data and ECG data are stored in processor memory or connected data recording equipment. When sufficient ultrasound images have been obtained from a particular viewing perspective, such as spanning several heartbeats, the clinician may rotate the transducer through a small angle to give it a new viewing perspective. Then the process of recording ultrasound images, transducer location/orientation data and ECG data is repeated until a sufficient number of images have been obtained. This process of rotating and imaging can be repeated until the catheter has been rotated through the entire angle of rotation required to image the desired volume of the patient's heart.

While gathering ultrasound images, the processor may generate and display a cartoon rendering of the ultrasound images at each viewing perspective in order to provide the clinician with a cartoon view of the structure being imaged. The clinician may then switch between viewing raw ultrasound data and viewing the cartoon rendered structure. Additionally, the clinician may direct the processor to correlate the cartoon rendered image to an external reference frame, such as the patient or examination table.

Once all of the ultrasound image data for the desired imaging volume has been obtained, the clinician may direct the processor to generate a three dimensional cartoon rendered image dataset. This dataset may be displayed for viewing by the clinician who may then use an interactive interface to select a particular portion for closer viewing. By viewing the selected display, the clinician may decide that additional images should be obtained, such as to improve the image clarity of a particular portion, or that the transducer should be repositioned in order to obtain images from a different perspective, such as to investigate a particular volume of interest not well imaged. The clinician may follow a similar procedure in obtaining the additional ultrasound images.

Once the ultrasound imaging procedure is over, the clinician may use the processor to interrogate the three-dimensional image dataset in order to assess the health of the patient's heart. For example, the clinician may use the interactive display in order to view various portions of the heart from different viewing angles and at different magnifications. The clinician may also use the processor to generate a four-dimensional view (i.e., moving three-dimensional image) by selecting ultrasound images for processing based upon the ECG signal at the time of each image. The various processing embodiments may be employed on images for processing based on ECG triggering in order to generate three-dimensional cartoon renderings at particular portions of the heartbeat cycle.

In each of the foregoing embodiments, image frames may be selected for processing based upon trigger events or like portions of ECG data so that cartoon rendered image frames correspond to like portions of the heartbeat cycle as well as approximately equal transducer rotational orientations. In such processing, the process steps illustrated in FIG. 10-14 may be repeated for each of different trigger events, or varying time delays after a recognizable trigger event (e.g., the R wave). In this manner, a three-dimensional cartoon rendered image can be generated for the heart at the time of a particular repeating trigger event or like portion of the ECG trace. Also, a four-dimensional (three spatial dimensions plus time) cartoon rendered image dataset can be generated for the heart spanning a portion or all of the heartbeat cycle.

In another embodiment, three-dimensional and four-dimensional image ultrasound image datasets generated according to various embodiments may be combined with image data from one or more external sources. For example, fluoroscopic images of the heart may be correlated to ultrasound images using time stamp or ECG data and thereby correlated to particular three-dimensional cartoon rendered ultrasound image datasets. Such correlated images then can be presented as overlapping or otherwise merged images on a display. Since the positions of the X-ray source and imaging plane are known within an external frame of reference, this composite display will show the cartoon rendered structures overlapping or otherwise fixed in the external frame of reference. This embodiment method may also enable clinicians to see structures outside of the ultrasound image scan (e.g., behind the transducer array or beyond the imaging range of the transducer) as they match up with ultrasound imaged structures. In this manner, the physician may locate the ultrasound images or the cartoon rendered images of heart structure with respect to ribs, vertebrae, implanted pacemakers and pacing leads, or other catheters (such as ablation catheters) that are imaged by fluoroscopy.

In another embodiment, externally applied ultrasound localizing equipment with fiducial references may be employed to locate the intracardiac catheter in two correlated coordinate systems. In this embodiment, three or more ultrasound transducers may be positioned on the patient at locations correlated to the external frame of reference. By imaging the catheter using the three or more external ultrasound transducers, the location of the catheter in three-dimensional space with respect to the external transducers can be determined by echo location. The processor can then locate the intracardiac ultrasound images within the external frame of reference by means of two coordinate transformations (image to external transducer frame of reference, and then external transducer frame of reference to the external frame of reference). An example of a system of localizing ultrasound transducers suitable for this method is provided in U.S. Pat. No. 5,515,853 which is hereby incorporated by reference in its entirety.

Each of the foregoing embodiment methods may be implemented on an ultrasound imaging system embodiment, including system elements described above with reference to FIG. 1, with the system processor adapted and configured by software instructions to perform the various method steps. Such implementing software instructions may be stored on computer readable memory accessed by the system processor, such as system read only memory within the processor, system random access memory within the processor, internal hard drive memory, external hard drive memory, including an external hard drive memory coupled to the system processor via a network, and/or a compact disc.

Another embodiment of the present invention is a computer readable memory having software instructions stored therein which will direct a processor to perform the method steps of the foregoing embodiment methods. Such a computer readable memory may be any storage medium connectable to a computer including, for example, read only memory, random access memory, internal hard drive memory, external hard drive memory, including an external hard drive memory coupled to and accessible via a network, and a compact disc.

While the present invention has been disclosed with reference to certain exemplary embodiments, numerous modifications, alterations, and changes to the described embodiments are possible without departing from the sphere and scope of the present invention, as defined in the appended claims. Accordingly, it is intended that the present invention not be limited to the described embodiments, but that it have the full scope defined by the language of the following claims, and equivalents thereof.

I claim:

1. A computer for use in intracardiac ultrasound imaging, comprising:
   a data connection for connecting to an ultrasound beamformer circuit; and
   a processor coupled to the data connection and configured with processor-executable instructions configured to cause the processor to perform operations comprising:
   storing a plurality of ultrasound image frames in memory;
   storing in memory a rotational orientation of an ultrasound transducer corresponding to each of the plurality of ultrasound image frames;
   detecting edges of tissue structures within each of the plurality of image frames;
   determining a spatial location of each of the detected edges in each of the plurality of image frames;
   statistically analyzing the spatial locations of the detected edges among a subset of the plurality of image frames with an approximately equal transducer rotational orientation to determine representative spatial locations for the tissue structures imaged from the approximately equal transducer rotational orientation;
   generating a cartoon rendered image frame of the tissue structures based upon the representative spatial locations imaged from the approximately equal transducer rotational orientation;
   repeating the operations of statistically analyzing the spatial locations of the detected edges and generating cartoon rendered image frames for each of a plurality of approximately equal transducer rotational orientations to generate a plurality of cartoon rendered image frames; and
   combining the plurality of cartoon rendered image frames using their corresponding approximately equal transducer rotation orientations to generate a three-dimensional cartoon rendering of tissue structure.

2. The computer of claim 1, wherein the processor is configured with processor-executable instructions configured to cause the processor to perform operations further comprising displaying the cartoon rendering of the tissue structures.

3. The computer of claim 1, wherein the processor is configured with processor-executable instructions configured to cause the processor to perform operations further comprising statistically analyzing spatial locations of detected edges among the plurality of image frames by determining an average location of the detected edges among the plurality of image frames.

4. The computer of claim 1, wherein the processor is configured with processor-executable instructions configured to cause the processor to perform operations further comprising:
   recognizing a tissue structure;
   matching the recognized tissue structure to a model of heart tissue structures; and
   back-calculating an imaging perspective of the ultrasound transducer based upon the results of matching the recognized tissue structure to the model of heart tissue structures.

5. The computer of claim 4, wherein the processor is configured with processor-executable instructions configured to cause the processor to perform operations further comprising registering the recognized tissue structure within an external coordinate reference frame.

6. The computer of claim 1, wherein the processor is configured with processor-executable instructions configured to cause the processor to perform operations further comprising:
   receiving and storing an electrocardiogram signal corresponding in time of recording to the plurality of ultrasound image frames;
   performing the operations of statistically analyzing the spatial locations of the detected edges among a subset of the plurality of image frames with an approximately equal transducer rotational orientation and generating a cartoon rendered image frame of the tissue structures based upon the representative spatial locations imaged from the approximately equal transducer rotational orientation for a subset of the plurality of image frames corresponding to a trigger event in the electrocardiogram signal; and combining the plurality of cartoon rendered image frames within the subset of the plurality of image frames corresponding to the trigger event in the electrocardiogram signal using their respective corresponding approximately equal transducer rotation orientations to generate a three-dimensional cartoon rendering of tissue structure corresponding to the trigger event.

7. The computer of claim 1, wherein the processor is configured with processor-executable instructions configured to cause the processor to perform operations further comprising:

receiving and storing an electrocardiogram signal corresponding in time of recording to the plurality of ultrasound image frames;

performing the operations of statistically analyzing the spatial locations of the detected edges among a subset of the plurality of image frames with an approximately equal transducer rotational orientation and generating a cartoon rendered image frame of the tissue structures based upon the representative spatial locations imaged from the approximately equal transducer rotational orientation for subsets of the plurality of image frames corresponding to like portions of the electrocardiogram signal; and combining the plurality of cartoon rendered image frames within each subset of the plurality of image frames corresponding to like portions of the electrocardiogram signal using their respective corresponding approximately equal transducer rotation orientations to generate a four-dimensional cartoon rendering of tissue structure.

8. The computer of claim 1, wherein the processor is configured with processor-executable instructions configured to cause the processor to perform operations further comprising:

presenting a graphical user interface configured to permit a user to indicate a portion of the three dimensional cartoon rendering of tissue structure to be displayed;

receiving user inputs indicating a portion of the three-dimensional cartoon rendering of tissue structure to be displayed; and generating a display corresponding to the user inputs.

9. A computer for use in intracardiac ultrasound imaging, comprising:

means for storing a plurality of ultrasound image frames;

means for storing a rotational orientation of an ultrasound transducer corresponding to each of the plurality of ultrasound image frames;

means for detecting edges of tissue structures within each of the plurality of image frames;

means for determining a spatial location of each of the detected edges in each of the plurality of image frames;

means for statistically analyzing the spatial locations of the detected edges among a subset of the plurality of image frames with an approximately equal transducer rotational orientation to determine representative spatial locations for the tissue structures imaged from the approximately equal transducer rotational orientation;

means for generating a cartoon rendered image frame of the tissue structures based upon the representative spatial locations imaged from the approximately equal transducer rotational orientation;

means for repeating the operations of statistically analyzing the spatial locations of the detected edges and generating cartoon rendered image frames for each of a plurality of approximately equal transducer rotational orientations to generate a plurality of cartoon rendered image frames; and means for combining the plurality of cartoon rendered image frames using their corresponding approximately equal transducer rotation orientations to generate a three-dimensional cartoon rendering of tissue structure.

10. The computer of claim 9, further comprising means for displaying the cartoon rendering of the tissue structures.

11. The computer of claim 9, further comprising means for statistically analyzing spatial locations of detected edges among the plurality of image frames by determining an average location of the detected edges among the plurality of image frames.

12. The computer of claim 9, further comprising:

means for recognizing a tissue structure:

means for matching the recognized tissue structure to a model of heart tissue structures; and means for back-calculating an imaging perspective of the ultrasound transducer based upon the results of matching the recognized tissue structure to the model of heart tissue structures.

13. The computer of claim 12, further comprising means for registering the recognized tissue structure within an external coordinate reference frame.

14. The computer of claim 9, further comprising:

means for receiving and storing an electrocardiogram signal corresponding in time of recording to the plurality of ultrasound image frames;

means for performing the operations of statistically analyzing the spatial locations of the detected edges among a subset of the plurality of image frames with an approximately equal transducer rotational orientation and generating a cartoon rendered image frame of the tissue structures based upon the representative spatial locations imaged from the approximately equal transducer rotational orientation for a subset of the plurality of image frames corresponding to a trigger event in the electrocardiogram signal; and means for combining the plurality of cartoon rendered image frames within the subset of the plurality of image frames corresponding to the trigger event in the electrocardiogram signal using their respective corresponding approximately equal transducer rotation orientations to generate a three-dimensional cartoon rendering of tissue structure corresponding to the trigger event.

15. The computer of claim 9, further comprising:

means for receiving and storing an electrocardiogram signal corresponding in time of recording to the plurality of ultrasound image frames;

means for performing the operations of statistically analyzing the spatial locations of the detected edges among a subset of the plurality of image frames with an approximately equal transducer rotational orientation and generating a cartoon rendered image frame of the tissue structures based upon the representative spatial locations imaged from the approximately equal transducer rotational orientation for subsets of the plurality of image frames corresponding to like portions of the electrocardiogram signal; and means for combining the plurality of cartoon rendered image frames within each subset of the plurality of image frames corresponding to like portions of the electrocardiogram signal using their respective corresponding approximately equal transducer rotation orientations to generate a four-dimensional cartoon rendering of tissue structure.

16. The computer of claim 9, further comprising:
means for presenting a graphical user interface configured to permit a user to indicate a portion of the three dimensional cartoon rendering of tissue structure to be displayed;
means for receiving user inputs indicating a portion of the three-dimensional cartoon rendering of tissue structure to be displayed; and
means for generating a display corresponding to the user inputs.

17. A method for processing a plurality of intracardiac ultrasound images stored in a computer readable memory that were obtained from an intracardiac ultrasound imaging catheter having a phased array ultrasound transducer, comprising:
receiving from the computer readable memory a plurality of ultrasound image frames and data indicating a transducer rotational orientation associated with each one of the plurality of ultrasound image frames;
detecting edges of tissue structures within each of the plurality of image frames;
determining a spatial location of each of the detected edges in each of the plurality of image frames;
statistically analyzing the spatial locations of the detected edges among a subset of the plurality of image frames with an approximately equal transducer rotational orientation to determine representative spatial locations for the tissue structures imaged from the approximately equal transducer rotational orientation;
generating a cartoon rendered image frame of the tissue structures based upon the representative spatial locations imaged from the approximately equal transducer rotational orientation;
repeating the steps of statistically analyzing the spatial locations of the detected edges and generating cartoon rendered image frames for each of a plurality of approximately equal transducer rotational orientations to generate a plurality of cartoon rendered image frames; and
combining the plurality of cartoon rendered image frames using their corresponding approximately equal transducer rotation orientations to generate a three-dimensional cartoon rendering of tissue structure.

18. The method of claim 17, further comprising displaying the cartoon rendering of the tissue structures.

19. The method of claim 17, wherein statistically analyzing spatial locations of detected edges among the plurality of image frames comprising determining an average location of the detected edges among the plurality of image frames.

20. The method of claim 17, wherein statistically analyzing spatial locations of detected edges among the plurality of image frames comprising determining a mean location of the detected edges among the plurality of image frames.

21. The method of claim 17, wherein statistically analyzing spatial locations of detected edges among the plurality of image frames comprising determining a weighted average location of the detected edges among the plurality of image frames.

22. The method of claim 17, further comprising:
recognizing a tissue structure;
matching the recognized tissue structure to a model of heart tissue structures; and
back-calculating an imaging perspective of the phased array ultrasound transducer based upon the results of matching the recognized tissue structure to the model of heart tissue structures.

23. The method of claim 22, further comprising registering the recognized tissue structure within an external coordinate reference frame.

24. The method of claim 17, further comprising:
receiving from computer memory an electrocardiogram signal corresponding in time of recording to the plurality of ultrasound image frames, wherein, the steps of statistically analyzing the spatial locations of the detected edges among a subset of the plurality of image frames with an approximately equal transducer rotational orientation and generating a cartoon rendered image frame of the tissue structures based upon the representative spatial locations imaged from the approximately equal transducer rotational orientation are performed for a subset of the plurality of image frames corresponding to a trigger event in the electrocardiogram signal; and
combining the plurality of cartoon rendered image frames within the subset of the plurality of image frames corresponding to the trigger event in the electrocardiogram signal using their respective corresponding approximately equal transducer rotation orientations to generate a three-dimensional cartoon rendering of tissue structure corresponding to the trigger event.

25. The method of claim 24, wherein the trigger event is a pacing pulse.

26. The method of claim 17, further comprising:
receiving from the computer memory an electrocardiogram signal corresponding in time of recording to the plurality of ultrasound image frames, wherein, the steps of statistically analyzing the spatial locations of the detected edges among a subset of the plurality of image frames with an approximately equal transducer rotational orientation and generating a cartoon rendered image frame of the tissue structures based upon the representative spatial locations imaged from the approximately equal transducer rotational orientation are performed for subsets of the plurality of image frames corresponding to like portions of the electrocardiogram signal; and
combining the plurality of cartoon rendered image frames within each subset of the plurality of image frames corresponding to like portions of the electrocardiogram signal using their respective corresponding approximately equal transducer rotation orientations to generate a four-dimensional cartoon rendering of tissue structure.

27. A method for displaying intracardiac ultrasound images stored in a computer readable memory that were obtained from an intracardiac ultrasound imaging catheter having a phased array ultrasound transducer, comprising:
receiving from the computer readable memory a plurality of ultrasound image frames and data indicating a transducer rotational orientation associated with each one of the plurality of ultrasound image frames;
detecting edges of tissue structures within each of the plurality of image frames;
determining a spatial location of each of the detected edges in each of the plurality of image frames;
statistically analyzing the spatial locations of the detected edges among a subset of the plurality of image frames with an approximately equal transducer rotational orientation to determine representative spatial locations for the tissue structures imaged from the approximately equal transducer rotational orientation;
generating a cartoon rendered image frame of the tissue structures based upon the representative spatial locations imaged from the approximately equal transducer rotational orientation;

repeating the steps of statistically analyzing the spatial locations of the detected edges and generating cartoon rendered image frames for each of a plurality of approximately equal transducer rotational orientations to generate a plurality of cartoon rendered image frames;

combining the plurality of cartoon rendered image frames using their corresponding approximately equal transducer rotation orientations to generate a three-dimensional cartoon rendering of tissue structure;

presenting a graphical user interface configured to permit a user to indicate a portion of the three-dimensional cartoon rendering of tissue structure to be displayed;

receiving user inputs indicating a portion of the three-dimensional cartoon rendering of tissue structure to be displayed; and generating a display corresponding to the user inputs.

* * * * *